(12) United States Patent
Keogh et al.

(10) Patent No.: US 11,998,177 B2
(45) Date of Patent: Jun. 4, 2024

(54) SCOPE

(71) Applicant: National University of Ireland, Galway, Galway (IE)

(72) Inventors: Ivan Keogh, Galway (IE); Rory O'Callaghan, Cavan (IE); Elizabeth McGloughlin, Limerick (IE); Martin Gallagher, Galway (IE); Christina Walsh, Galway (IE)

(73) Assignee: National University of Ireland, Galway, Galway (IE)

( * ) Notice: Subject to any disclaimer, the term of this patent is extended or adjusted under 35 U.S.C. 154(b) by 199 days.

(21) Appl. No.: 17/436,960

(22) PCT Filed: Mar. 5, 2020

(86) PCT No.: PCT/EP2020/055944
§ 371 (c)(1),
(2) Date: Sep. 7, 2021

(87) PCT Pub. No.: WO2020/178407
PCT Pub. Date: Sep. 10, 2020

(65) Prior Publication Data
US 2022/0167841 A1 Jun. 2, 2022

(30) Foreign Application Priority Data

Mar. 6, 2019 (EP) .................................. 19161096

(51) Int. Cl.
*A61B 1/227* (2006.01)
*A61B 1/04* (2006.01)
*A61B 1/06* (2006.01)
*A61G 13/12* (2006.01)

(52) U.S. Cl.
CPC ................ *A61B 1/227* (2013.01); *A61B 1/04* (2013.01); *A61B 1/06* (2013.01); *A61G 13/121* (2013.01)

(58) Field of Classification Search
CPC ........................................................ A61B 1/227
USPC ................................................... 600/188–245
See application file for complete search history.

(56) References Cited

U.S. PATENT DOCUMENTS

| | | | |
|---|---|---|---|
| 3,146,775 A * | 9/1964 | Moore | A61B 1/227 385/115 |
| 10,765,309 B1 * | 9/2020 | Alsaifi | A61B 1/00089 |
| 2011/0134234 A1 * | 6/2011 | Kim | G02B 21/0008 348/80 |

(Continued)

FOREIGN PATENT DOCUMENTS

| | | |
|---|---|---|
| JP | 2017-63812 A | 4/2017 |
| KR | 2018-0029788 A | 3/2018 |
| WO | 2018/197870 A1 | 11/2018 |

OTHER PUBLICATIONS

International Search Report and Written Opinion issued in International Application No. PCT/EP2020/055944, dated Sep. 10, 2020, 15 pages.

*Primary Examiner* — Eduardo C Robert
*Assistant Examiner* — Tara Rose E Carter
(74) *Attorney, Agent, or Firm* — Brown Rudnick LLP; Adam M. Schoen

(57) ABSTRACT

A scope (1) for examining or surgically treating ears comprising at least one camera (6), a light source (7), and a stabilizer (2) for supporting the camera (7) in or on the stabilizer (2), the stabilizer (2) being integral with the camera (7) and being configured to stabilize the scope (1) in an ear canal.

27 Claims, 32 Drawing Sheets

(56) References Cited

U.S. PATENT DOCUMENTS

2016/0374546 A1* 12/2016 Berbee .................... A61B 1/05
                                                    600/109
2017/0245889 A1    8/2017  Herrell et al.
2018/0125345 A1    5/2018  Rebella et al.
2018/0228358 A1    8/2018  Hall

* cited by examiner

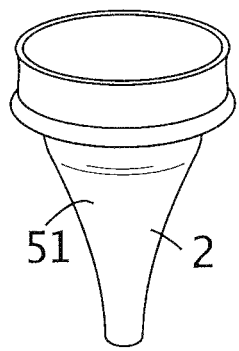 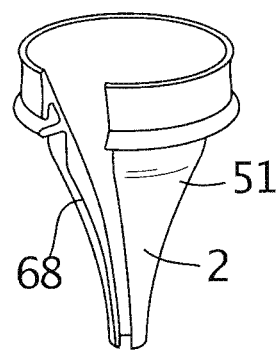 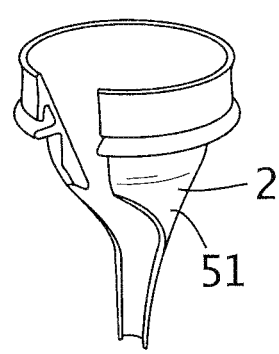
Fig. 16(a)   Fig. 16(b)   Fig. 16(c)
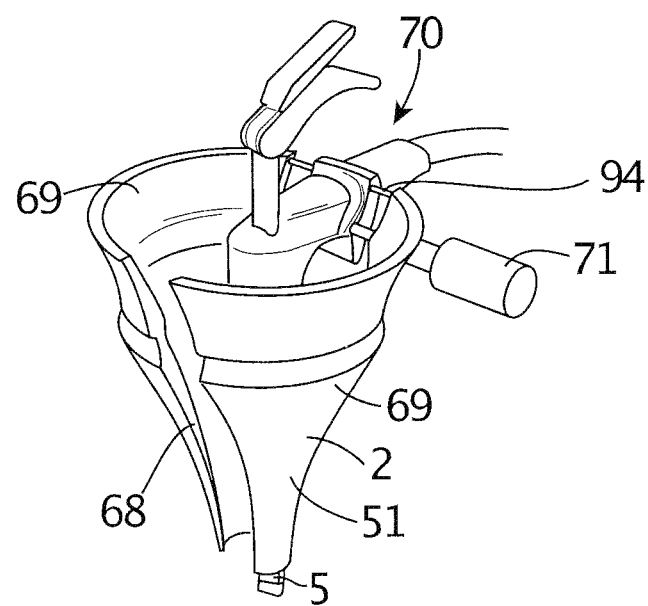
Fig. 17

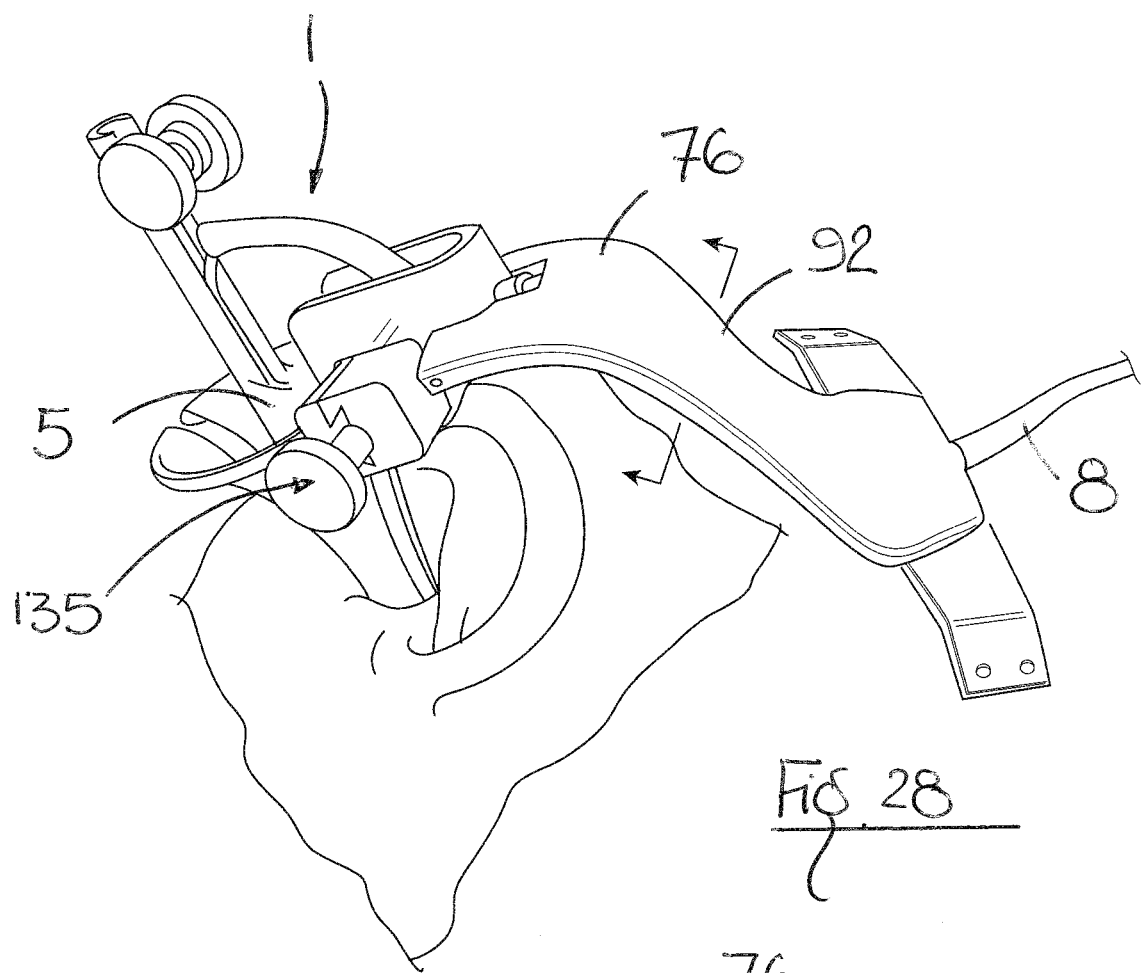
Fig. 28
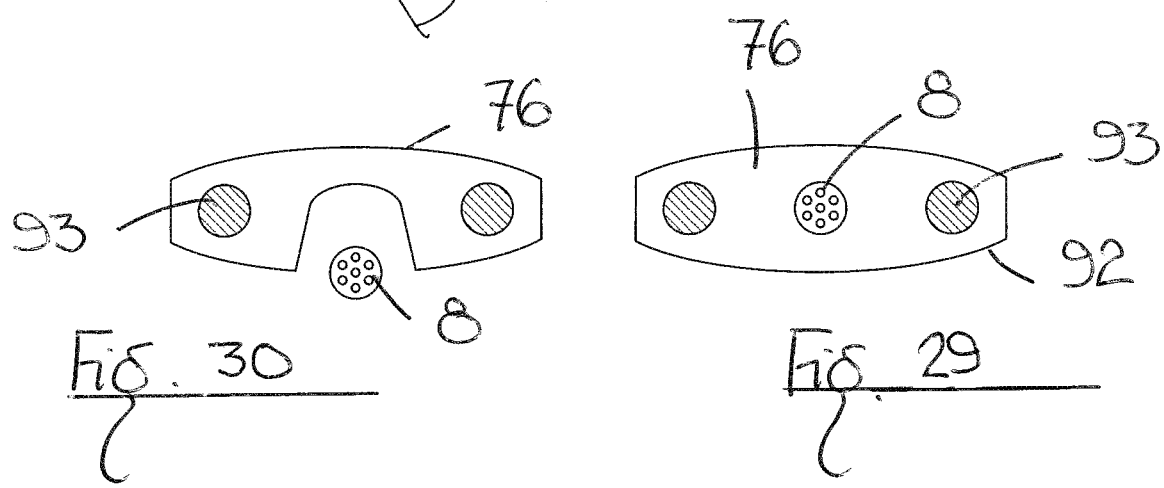
Fig. 30
Fig. 29

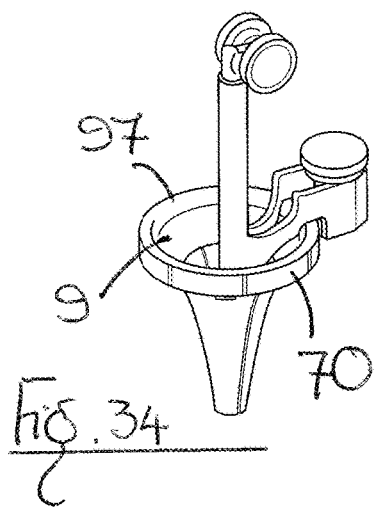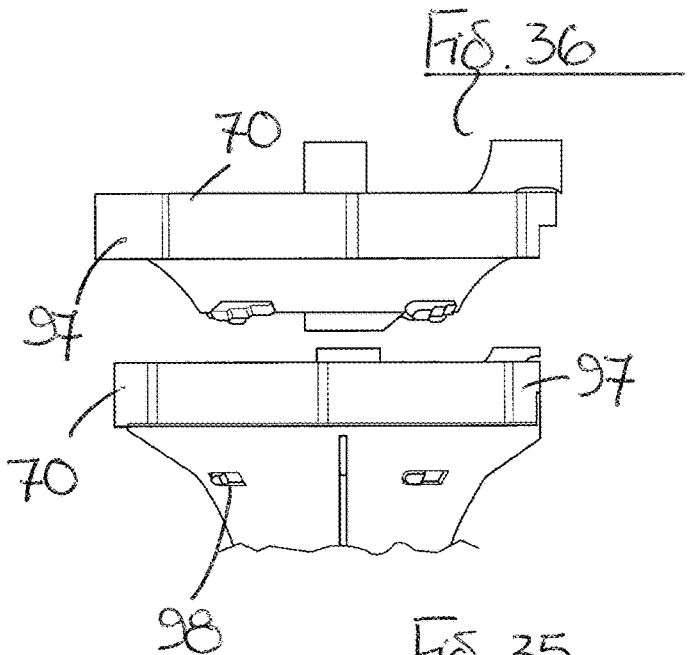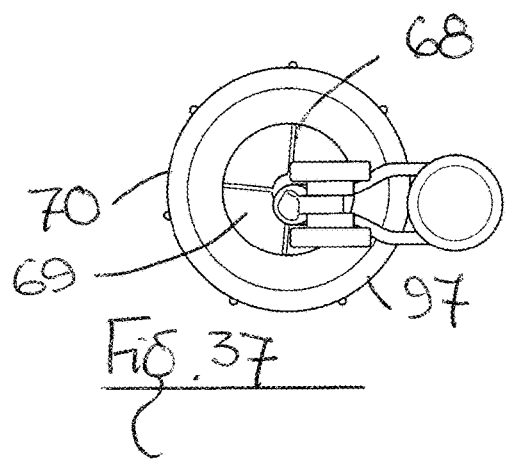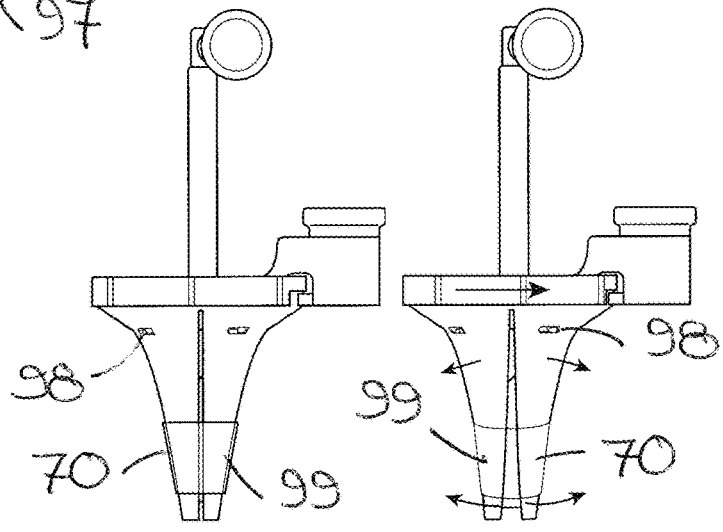

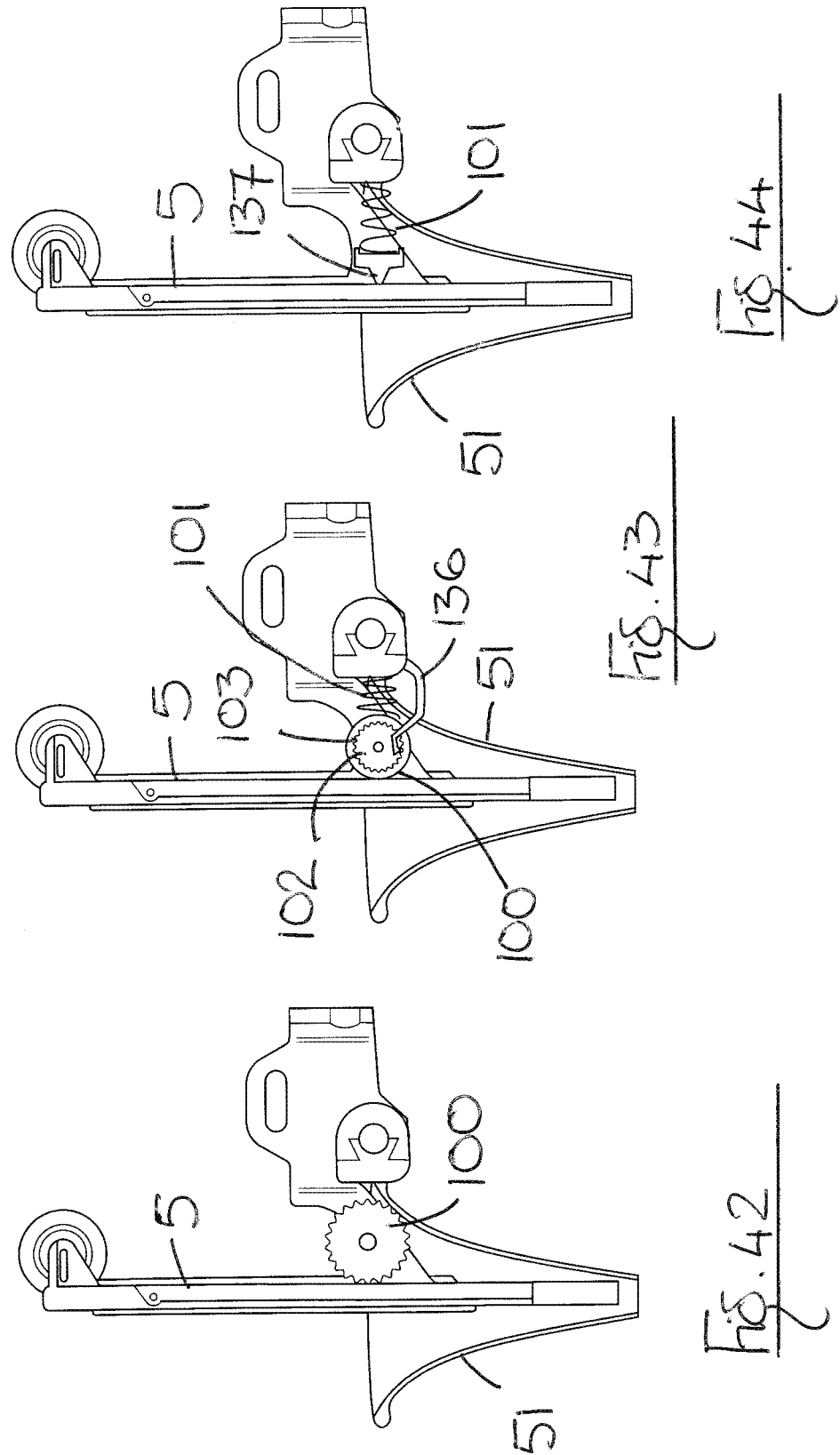

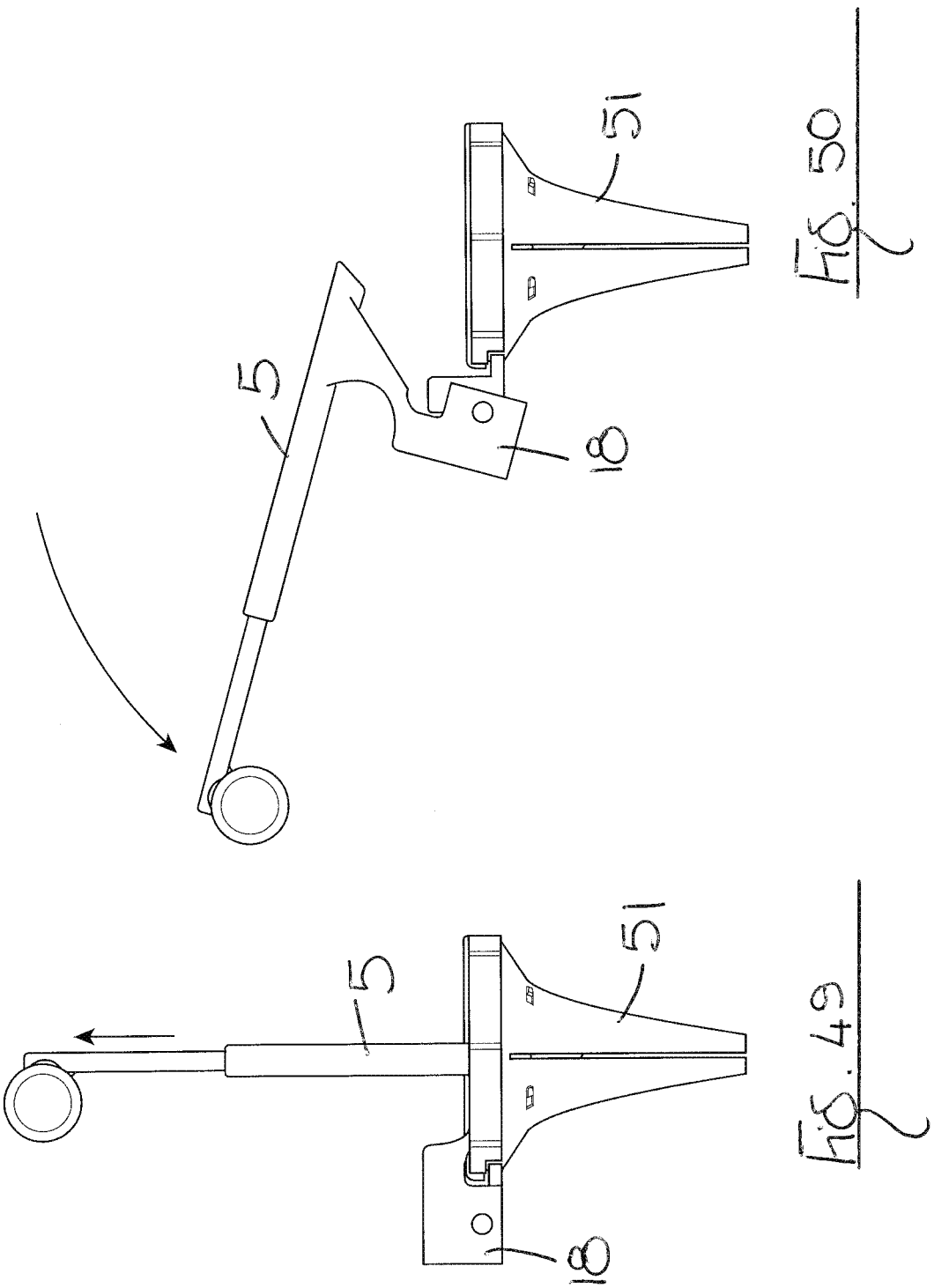

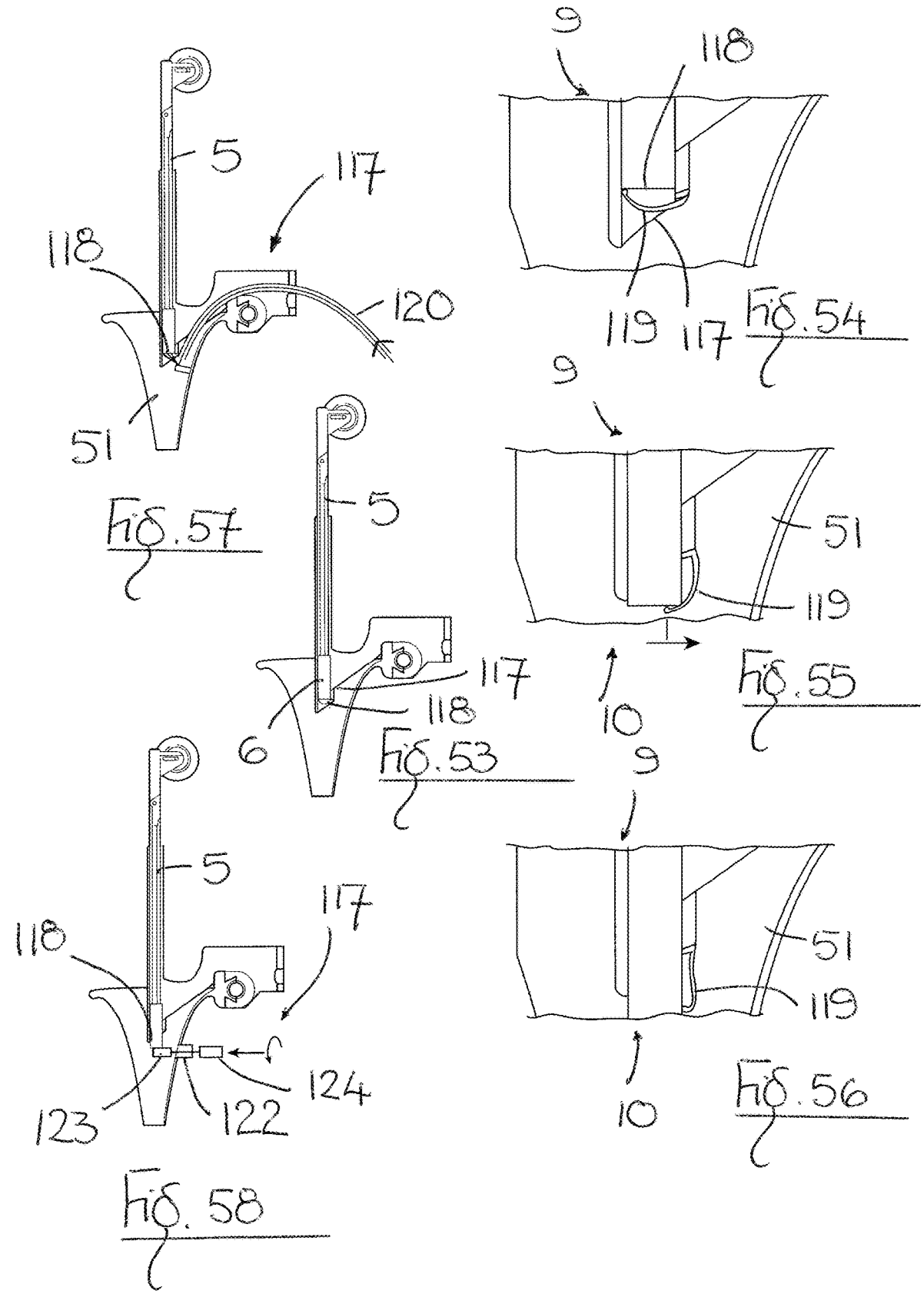

SCOPE

INTRODUCTION

This invention relates to a scope and more particularly to a medical scope such as an otoscope or an endoscope for examining and surgically treating ears.

BACKGROUND OF THE INVENTION

Medical devices of various types are employed to examine and perform surgery on ears. For example, endoscopes and otoscopes (hereinafter referred to collectively as scopes) are instruments which are held against the eye to view and magnify the subject. These instruments have evolved with the addition of a camera so that the subject is viewed using a computer monitor or a video display.

Recurrent acute otitis media, otitis media with effusion, chronic secretory/suppurative otitis media continues to impact quality of life for millions of patients world-wide. Hearing loss, complications of inflammation and complications of treatment are daily challenges and, as a result, patients with these conditions (children and adults) frequently require invasive ear surgery. As ears are wrapped in dense bone, surgical access and visualization are essentials for safe ear surgery In traditional ear surgery, microscopic visualization is employed with a dynamic bi-manual surgical technique. However, a major disadvantage of this approach is the narrow field of view looking down into the ear canal which can lead to poorer visualization of disease in difficult to access areas in the middle ear, such as the sinus tympani and facial recess.

In order to improve the field of view, it is often necessary to expose the middle ear and attic area by performing a mastoidectomy. However, mastoidectomy procedures are associated with increased operating times, more serious complications, longer hospital stays and protracted recovery for patients.

In addition, trans canal surgery is generally performed through a speculum by looking through the microscope and using specialized instruments resulting in a narrow field of view. The dynamic two-handed approach used in microscopic surgery is where the surgeon balances the speculum within the patient's ear canal and keeps it in position with at least one finger while still maintaining the capability of using their two hands for use of surgical tools. The approach means that the surgeon can change tool while maintaining the position of the second tool and the speculum.

Moreover, due to the large size of the microscopic equipment employed in ear surgeries, negative ergonomic issues arise—the surgeon is forced into an extended position due to the size of the operating microscope which can compromise the dexterity required of the surgeon during surgical procedures.

More recently, a single-handed endoscope assisted technique has gained popularity as an alternative to microscopic methods. However, although the views achieved with an endoscope are far superior, using one hand to perform middle ear surgery is challenging and can require reskilling of the surgeon to perform a single-handed technique.

Moreover, due to the presence of the camera on scopes such as endoscopes, the centre of gravity of the unit is shifted towards the proximal end while the shift in the centre of gravity towards the proximal end is particularly pronounced in long rigid endoscopes of the type employed in ear surgery.

The proximal shift in the centre of gravity has negative implications when deploying endoscopes in ear surgery whilst simultaneously trying to maintain a two-handed technique. In order to address the shift in the centre of gravity, it is known to employ an endoscope stand or to connect the endoscope to a speculum which must then be attached to a speculum stand which is fixed to a solid structure such as a bed. However, such devices can be cumbersome and still fail to address problems associated with the shift in the centre of gravity. Moreover, where the endoscope length is reduced to avoid a shift in the centre of gravity, the video camera head can obstruct access while although a longer endoscope can alleviate this problem, the longer endoscope has the consequence of moving the centre of gravity further away from the stand resulting in increased leverage which can overpower the strength of locking mechanisms and friction grips, keeping the speculum and scope in place.

Finally, when using traditional analogue otoscopes or endoscopes, the human eye is effectively the image sensor utilizing the magnification provided by the otoscope/endoscope optics. Accordingly, when the otoscope/endoscope is reoriented or rotated in the ear canal the image observed remains oriented with respect to the user (independent of the otoscope/endoscope). However, with a video otoscope or endoscope the image sensor is located on the scope. Accordingly, when the scope is reoriented or rotated (perhaps for the comfort of the patient) the image observed also reorients or rotates which can result in disorientation of the user.

An object of the invention is to overcome at least some of the problems of the prior art.

SUMMARY OF THE INVENTION

According to the invention there is provided a scope for examining or surgically treating ears comprising:
- at least one camera; and
- a stabilizer for supporting the camera in or on the stabilizer, the stabilizer being configured to stabilize the scope in an ear canal wherein the scope is configured to maintain its centre of gravity within the volume contained within the stabilizer.

Preferably, the scope further comprises a light source. Suitably, the light source is a direct light or conduit piping in light.

In one embodiment, the stabilizer is integral with the camera. Preferably, the camera is provided on a probe mountable on the stabilizer at a probe mounting. More preferably, the stabilizer comprises a speculum holder. Most preferably, the stabilizer comprises a detachable or integrated speculum.

Suitably, the speculum comprises a proximal open end, a distal insertion end, a substantially conical wall extending between the proximal open end and the distal end and a volume contained within the speculum is defined between the open end and the distal insertion end.

In a preferred embodiment, the speculum comprises a weight-balanced speculum.

Preferably, the weight-balanced speculum comprises increased weight below its centre of gravity. Suitably, the weight-balanced speculum comprises a combination of low density and high density material.

Preferably, the low density material comprises a polymer. More preferably, the low density material is disposed towards the proximal end of the speculum.

Suitably, the high density material is disposed towards the distal end of the speculum. Preferably, the high density material comprises a metal material.

Suitably, the centre of gravity of the scope is located within the volume contained within the speculum by a balancing weight to balance the weight of the probe.

Preferably, the balancing weight is attached to or integral with the speculum and/or the probe.

Optionally, the balancing weight is located on the speculum holder.

Preferably, the centre of gravity of the scope is located within a volume contained within the speculum by at least one laterally extending wing or arm on the scope.

Suitably, the probe mounting comprises a probe moving mechanism. Preferably, the probe moving mechanism comprises a probe sliding mechanism. More preferably, the probe sliding mechanism is configured to move the probe proximally and distally.

Suitably, the probe moving mechanism comprises a friction mounting defined between the stabilizer and the probe. Preferably, the friction mounting comprises a low friction mounting.

In one embodiment, the probe mounting comprises a hinged probe mounting.

Suitably, the probe is curved or conformable with at least a portion of a contour of the speculum.

Optionally, the probe is rotatably mountable in the probe mounting to change the angle of view of the camera.

Preferably, the scope comprises a flexible section for flexibly supporting the probe.

In one embodiment, the scope further comprises an image orienting mechanism to orient the image from the camera relative to the user.

Preferably, the image orienting mechanism comprises at least one gyroscope and/or at least one tilt switch.

In one embodiment, the probe is detachable from the stabilizer.

Preferably, the probe is laterally movable in the stabilizer More preferably, the probe is laterally movable in the stabilizer in an in, out and side to side direction.

Suitably, the probe is self-locking. More preferably, the self-locking probe is rotatably lockable about its longitudinal axis to lock the probe.

In one embodiment, the self-locking probe comprises a non-uniform cross-section.

In a preferred embodiment, the probe comprises a depth control mechanism. Preferably, the depth control mechanism comprises a lockable depth control mechanism or a stop feature to control the depth of insertion of the probe. More preferably, the lockable depth control mechanism comprises at least one defined insertion limit. Optionally, the depth control mechanism comprises a shutter releasable type mechanism.

Advantageously, the depth control mechanism comprises an override function.

Optionally, the depth control mechanism comprises a haptic feedback. Preferably, the haptic feedback comprises a wheel, cog or pawl contactable with the probe.

In one embodiment, the speculum comprises an additional lumen or channel/hose for suction or for directing air or fluids towards the ear as required.

In a preferred embodiment, the speculum comprises a cut or cutaway portion through a sidewall of the speculum. Preferably, the speculum comprises two or more oppositely disposed cutaway portions or cuts through a sidewall of the speculum to define two or more expandable and contractable speculum blades.

Optionally, the probe is movable with at least one of the speculum blades. Preferably, the scope comprises an expansion mechanism to control movement of the blades.

In one embodiment, the expansion mechanism comprises an adjustment ring on the speculum. Preferably, the adjustment ring comprises graduations with each graduation corresponding with a speculum size.

In another embodiment, the expansion mechanism comprises a band of resilient material on the speculum.

Optionally, the scope comprises first and second oppositely disposed support arms to hold a camera module.

The invention also extends to a scope as hereinbefore defined further comprising an ear clip. Preferably, the ear clip embraces the ear and comprises a curved flexible arm.

In another embodiment, the invention also extends to a scope as hereinbefore defined further comprising an ear cup. Preferably, the ear cup surrounds the ear and comprises a downwardly concaved shape. Suitably, the scope further comprises a joint at the ear cup. Preferably, the joint comprises a ball joint through which the stabilizer connects to the ear cup.

The invention also extends to a scope as hereinbefore defined comprising a built-in camera cleaning unit. Preferably, the camera cleaning unit comprises a wiping blade/pad. Optionally, the camera cleaning unit comprises an irrigation or suction channel.

Alternatively, the camera cleaning unit comprises a manually slidable pad or brush.

In a preferred embodiment, the self-cleaning unit comprises a directional baffle or channel.

In another embodiment of the invention, the scope further comprises a data cable.

Preferably, the data cable comprises an anchor weight to minimize forces on the scope.

In one embodiment, the data cable comprises a cable extension. Alternatively, the data cable comprises a coiled cable. Alternatively, the data cable comprises a shape set cable.

In a preferred embodiment of the invention, the scope comprises an endoscope or an otoscope.

The invention also extends to a scope system comprising a scope as hereinbefore defined and a scope holder.

Preferably, the scope holder comprises a mounting plate and a positioning plate for aligning the scope. Suitably, the plate defines a central axis so that the speculum is centrally located within the mounting plate.

Preferably, the mounting plate is supported by the positioning plate via one or more arms extending from the scope.

More preferably, at least one arm extends from the speculum to the mounting plate.

Suitably, the scope is aligned with the mounting plate at a fastening acting between the arm and the mounting plate.

Optionally, the fastening is magnetic. Alternatively, the fastening is a slot along the mounting plate and the arm.

Advantageously, the mounting plate comprises a part-spherical mounting plate.

In one embodiment, the scope holder is deformable. Preferably, the deformable scope holder has a plasticity to allow reversible deformation of the scope holder.

In one embodiment, the deformable scope holder is integral with a data cable extending through the scope holder to form a scope holder cum data cable for simultaneously holding the scope in place during surgery and transmitting data.

In another embodiment, the invention also extends scope system as hereinbefore defined further comprising a headrest device for supporting a patient's head wherein the headrest device is self-adjusting in response to patient head movement.

Preferably, the headrest device comprises a headrest and a scope stand co-operable with the headrest to move in response to headrest movement to automatically re-position a scope held in the scope stand. More preferably, the headrest has an upper face having a flat surface.

Most preferably, the headrest comprises a convex lower face which allows the headrest to follow a patient's head movements.

Advantageously, a lower articulated arm extends between the headrest and the stand.

Preferably, the lower articulated arm extends between the headrest and a stand upright.

Optionally, the stand upright is provided with an upper articulated arm which projects from the stand upright towards the headrest. Preferably, the upper articulated arm comprises lockable sliding and tilting sections.

The invention also extends to a method of examining the external and middle ear during surgery comprising: placing a scope into the ear canal, the scope comprising at least one camera and a stabilizer for supporting the camera in or on the stabilizer, the stabilizer being configured to stabilize the scope in the ear canal wherein the scope is configured to maintain its centre of gravity within a volume contained within the stabilizer during treatment.

employing a dynamic two-handed technique, and viewing a camera feed from the scope while retaining the scope within the ear canal.

Preferably, the scope is used while a surgeon using the scope holds two surgical tools at the same time.

Suitably, the tools comprise at least two of: suctions; cutting tools; irrigation tools, perforation tools; holding tools; forceps; drills; lasers; and surgical curettes.

In one embodiment, the stabilizer comprises a speculum.

Suitably, the method further comprises adjusting the size of the speculum after the scope is placed to allow maximum operating space.

The method suitably comprises movement of the probe to allow maximum operating space for placing tools on both sides of the probe or multiple tools on one side.

Preferably, the size of the speculum is adjusted by choosing a speculum from a range of sizes and attaching onto the scope.

Optionally, the size of the speculum is adjusted by using an adjustable speculum which allows the user to expand the speculum within the ear canal.

Preferably, the size of the speculum is adjusted by using an adjustable speculum which automatically expands within the patient's ear canal.

Optionally, the method further comprises attaching the scope to a holder.

Suitably, the scope is attached onto a patient headband or glasses.

Optionally, the scope is attached to the patient's head. Alternatively, the scope is attached onto the patient's pillow. Alternatively, the scope is attached to the operating table.

Preferably, the holder is attached by clips, glue, sutures, stitches, tape or screws.

In one embodiment, the method comprises weighting the speculum and holder to maintain equilibrium within the ear.

In another embodiment, the method comprises bending the speculum to shape.

Preferably, the camera feed is viewed through a monitor, a projector or a video feed on the scope.

In another embodiment, the method comprises using 3D glasses to see depth perception.

Suitably, the method comprises using binocular cameras.

Preferably, the camera is provided on a probe mountable on the stabilizer at a probe mounting.

In one embodiment, the method comprises operating the probe by pushing the probe up and down. Alternatively, the method further comprises operating the probe by twisting handles on the probe. Alternatively, the method further comprises operating the probe by squeezing a lever to position the probe. Alternatively, the method comprises operating the probe by a screwing and unscrewing motion of the probe.

Suitably, the probe comprises a depth control mechanism.

Preferably, the depth control mechanism comprises a stop feature to control the depth of insertion of the probe. More preferably, the stop feature is overridden by pressing a feature down to allow the probe to continue working.

Optionally, the stop feature is overridden by twisting the probe to allow it to move past a safety point. Alternatively, the stop feature is overridden by using greater force to adjust the probe past a safety point. Alternatively, the stop feature is overridden by clicking the feature off to allow the probe to continue working.

Suitably, the method comprises adjusting the probe along a horizontal plane by sliding the probe left and right. Preferably, the method comprises adjusting the probe along a horizontal plane by releasing a stop feature and the probe moving right and left.

Alternatively, the method comprises adjusting the probe along a horizontal plane by screwing and unscrewing the probe to move along the horizontal plane. Alternatively, the method comprises adjusting the probe along a horizontal plane by electrically clicking a button for the probe to adjust to a desired position. Alternatively, the method comprises adjusting the orientation of the probe by software automatically rotating an image from the camera. Alternatively, the method comprises adjusting the orientation of the probe by twisting or pulling an orientation handle which allows a user to choose where they would like the top of an image to be. Alternatively, the method comprises the orientation of the probe by a user clicking a stop feature off and then adjusting the orientation.

The invention also extends to a method comprising cleaning the scope by removing the probe and cleaning the lens with a cleaning wipe in the scope. Alternatively, the method comprises cleaning the scope by putting suction or irrigation through the scope to clean the lens. Alternatively, the method comprises cleaning the scope by twisting the camera to clean the lens. Alternatively, the method comprises cleaning the scope by removing the scope and manually cleaning the lens.

In one embodiment, a user cleans the camera by spraying fluid towards a baffle or channel which redirects towards the camera cleaning it in the process. Optionally, fluid is sprayed through an internal channel which is part of the scope. Preferably, the fluid is sprayed from an irrigation tool and redirected to clean the camera using the baffle or channel.

The invention also extends to a method comprising determining the depth of the probe relative to the speculum via feedback provided through indexing which is felt through hepatic feedback through or sound, Optionally, the method comprises reading the depth of the probe relative to the speculum via a digital display through feedback and displaying the result on a screen.

Therefore, the invention provides a scope for examining or surgically treating ears comprising:

at least one camera;

a light source, and a stabilizer for supporting the camera in or on the stabilizer, the stabilizer being integral with the camera and being configured to stabilize the scope in an ear canal.

Suitably, the camera is provided on a probe mountable on the stabilizer at a probe mounting. Alternatively, the camera and the light source are integral with the stabilizer.

Preferably, the stabilizer comprises a speculum holder. More preferably, the stabilizer comprises a detachable or integrated speculum.

Advantageously, the scope is configured to maintain its centre of gravity within the volume contained within the speculum. In one embodiment, the centre of gravity of the scope is located within the speculum by a balancing weight to balance the weight of the probe. Preferably, the balancing weight is located on the speculum. Alternatively or in addition, the balancing weight is located on the speculum holder.

Optionally, the centre of gravity of the scope is located within the volume contained within the speculum by at least one laterally extending wing or arm on the scope wherein the volume is contained within the speculum is defined between the open end and the distal insertion end.

Preferably, the probe mounting comprises a probe sliding mechanism.

Suitably, the probe is curved or conformable with at least a portion of the contour of a speculum and is rotatably mountable in the probe mounting to change the angle of view of the camera.

Preferably, the scope comprises a flexible section on the scope for flexibly supporting the probe.

Advantageously, the scope further comprises an image orienting mechanism to orient the image from the camera relative to the user. In one embodiment, the image orienting mechanism comprises a gyroscope and/or a tilt switch. Suitably, the image orienting mechanism comprises a plurality of gyroscopes and/or tilt switches.

In one embodiment, the probe is detachable from the stabilizer.

Preferably, the speculum comprises one or more lumen or channels for suction or for directing air or fluids towards the ear as required. Alternatively the channels may be used for cleaning of the lens using suction, irrigation or cleaning.

Suitably, the speculum comprises two or more oppositely disposed cutaway portions to define two or more expandable and contractable speculum blades and the probe is optionally movable with at least one of the speculum blades. In another embodiment, the speculum comprises a wall having a single cutaway portion.

In a preferred embodiment of the invention, the scope comprises an endoscope or an otoscope.

The invention also extends to scope system comprising a scope as hereinbefore defined and a scope holder. Preferably, the scope holder comprises a mounting and positioning plate for aligning the scope, preferably a hemispherical or part spherical mounting plate Preferably, the scope is centred within a notional circle defined by the hemispherical mounting plate so that the speculum is centrally located within the hemispherical mounting plate. Advantageously, the centre point of the notional hemispherical sphere defined by the mounting plate, and optionally the notional hemispherical sphere defined by the mounting plate, aligns with a distal insertion end of the speculum.

In one embodiment, the hemispherical mounting plate is attached to the scope via one or more wing-like arms. Suitably, at least one arm extends between the peripheral hemispherical mounting plate and the speculum.

Preferably, the scope is aligned with the hemispherical mounting plate at an attachment actuator defined between the arm and the mounting plate. In one embodiment, the attachment actuator is magnetic. In an alternative embodiment, the attachment actuator can be a slot along the mounting plate and the arm.

In a further embodiment, the invention also extends to a headrest device for supporting a patient's head wherein the headrest device is self-adjusting in response to patient head movement. The headrest device can be employed with conventional surgical scopes and speculum or with the scope as hereinbefore defined to provide a system comprising the scope and the headrest.

Preferably, the headrest device comprises a headrest and a scope stand co-operable with the headrest to move in response to headrest movement to automatically re-position a scope held in the scope stand.

Suitably, the headrest device is adapted for use with the scope holder as hereinbefore defined.

Advantageously, the upper face of the headrest has a flat surface. Preferably, the headrest comprises a convex lower face which allows the headrest to follow a patient's head movements.

In one embodiment, a lower articulated arm extends between the headrest and the stand. Preferably, the lower articulated arm extends between the headrest and a stand upright. More preferably, the stand upright is provided with an upper articulated arm which projects from the stand upright towards the headrest.

In one embodiment, the upper articulation arm comprises lockable sliding and tilting sections.

Preferably, the upper articulated arm is provided with a scope mounting plate to which a flexible arm can be mounted for attaching to the scope or a scope holder.

This invention provides a weight balanced stabilized and self-supporting platform for performing minimally invasive middle ear surgeries, reducing admission times, potentially reducing complication rates and improving outcomes. The device of the invention facilitates endoscopic visualization while maintaining a traditional bi manual technique and is particularly suitable for use in routine and complex ear surgeries such as tympanoplasty (repair of the ear drum), middle ear exploration, cholesteatoma resection, ossicular chain reconstruction, stapes surgery and the like.

The weight balanced devices of the invention also maintain a low centre of gravity, lying within the space occupied by a traditional speculum to allow the scope to balance in the ear (even just on a momentary basis) without needing to be constantly held and therefore allowing for dynamic two-handed surgery.

The scope holder of the invention facilitates the easy positioning and re-positioning of the scope while the self-adjusting headrest device of the invention automatically re-positions speculum and scopes during surgery in accordance with patient movements to improve the ease or surgical procedures thus obviating the need for a surgeon to re-position the equipment.

BRIEF DESCRIPTION OF THE DRAWINGS

The invention will now be described, by way of example only, with reference to the accompanying drawings in which:

FIGS. 16(a) to 16(c) are perspective views from above and one side of various speculum types suitable for use with the scope of the invention in which the wall of the speculum can be continuous (a full speculum), cutaway (a straight cut speculum) or profiled (a profiled speculum) to facilitate easy removal of instruments and access to the superior ear canal;

FIG. 17 is a perspective view from above and one side of an eleventh embodiment of the invention in which the speculum of the scope of FIG. 16(b) is provided with two oppositely disposed cutaway portions to define two oppositely disposed speculum blades which can be expanded and contracted at the cutaways via an expansion mechanism, preferably which runs on guide pins;

FIG. 28 is a perspective view from above and one side of a further scope system of the invention made up of a scope and an alternative scope holder in which the scope holder is a deformable scope holder having a plasticity which allows reversible deformation of the scope holder;

FIG. 29 is a cross-sectional view through the scope holder of FIG. 28 with the data cable integrated in the deformable scope holder;

FIG. 30 is a cross-sectional view through a variant of the scope holder of FIGS. 28 and 29 in which the data cable is separate from the deformable scope holder;

FIG. 34 is a perspective view from above and one side of an alternative embodiment of the invention in which the speculum is provided with four blades and an adjustment ring for opening and closing the blades in graduated steps corresponding with different speculum sizes;

FIG. 35 is a side elevation of a portion of the speculum of the scope of FIG. 34;

FIG. 36 is an alternative side elevation of a portion of the speculum of the speculum of the scope of FIG. 34;

FIG. 37 is a top plan view of the scope of FIG. 34;

FIG. 38 is a side elevation of an alternative embodiment similar to FIGS. 34 to 37 but in which the expansion mechanism is in the form of a resilient material such as an elastomer over the speculum blades with the blades in a contracted or closed position;

FIG. 39 is an alternative side elevation of the scope of FIG. 38 with the blades expanding to an open position;

FIG. 42 is a side elevation of the scope of FIG. 40 in which the probe depth control actuator mechanism gives haptic feedback to a user via a cog in contact with the probe;

FIG. 43 is a side elevation of a variant of the scope of FIG. 40 in which the probe depth control actuator mechanism gives haptic feedback to a user via a wheel which is optionally in communication with the probe under the force of a spring and optionally the wheel has internal gear teeth indexing with a pawl so that when the gear teeth overcome the pawl feedback is given in the form of feel and/or a clicking sound;

FIG. 44 is a side elevation of a further variant of the scope of FIG. 40 in which the probe depth control actuator mechanism gives haptic feedback to a user via a pawl and ratchet holding or in contact with the probe;

FIG. 49 is a side elevation of a further embodiment of the invention in which probe mounting is hinged to allow for hinged removal of the probe from the speculum with the probe in a vertical position and being slidably removable from the speculum in the direction indicated by the arrow;

FIG. 50 is a side elevation of the scope of FIG. 49 with the probe removed from the speculum attached by the hinge in the direction indicated by the arrow;

FIG. 53 is a side elevation of a further embodiment of the invention provided with a built-in camera cleaning unit for cleaning the camera surface;

FIG. 54 is an enlarged side elevation of the built-in camera cleaning unit of FIG. 53 with the probe and camera surface disposed towards the proximal end of the speculum;

FIG. 55 is an enlarged side elevation of the built-in camera cleaning unit of FIG. 53 with the probe and camera surface moving towards the distal end of the speculum through the cleaning unit;

FIG. 56 is an enlarged side elevation of the built-in camera cleaning unit of FIG. 53 with the probe and camera surface disposed towards the proximal end of the speculum having been cleaned;

FIG. 57 is a side elevation of a scope of the invention with an alternative built-in camera cleaning unit, such as a channel or baffle having a suction or irrigation channel;

FIG. 58 is a side elevation of an alternative embodiment of the invention in which the built-in camera cleaning unit is a manually operable cleaning pad which is slidable across the camera face;

DETAILED DESCRIPTION OF THE INVENTION

Figure 1:
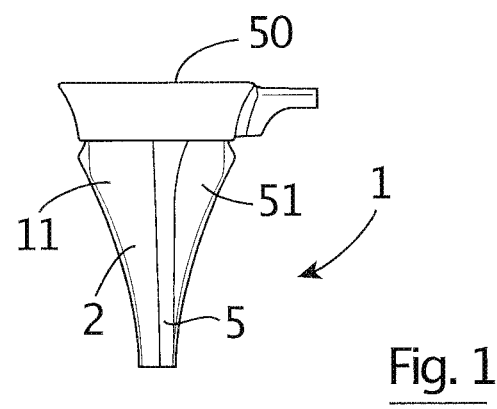
FIG. 1 is a side elevation of a first embodiment of a scope of the invention in the form of an endoscope made up of a camera probe and a stabilizer including a speculum integral with the camera probe to define a unitary speculum-probe endoscope which allows for bi-manual surgical techniques.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

Exemplification

Figure 2:
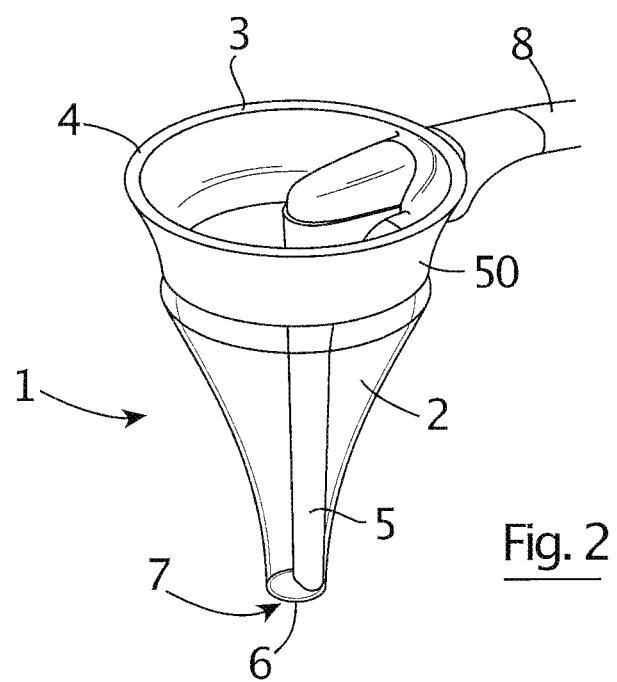
FIG. 2 is a perspective view from above and one side of the endoscope of FIG. 1.
Figure 3:
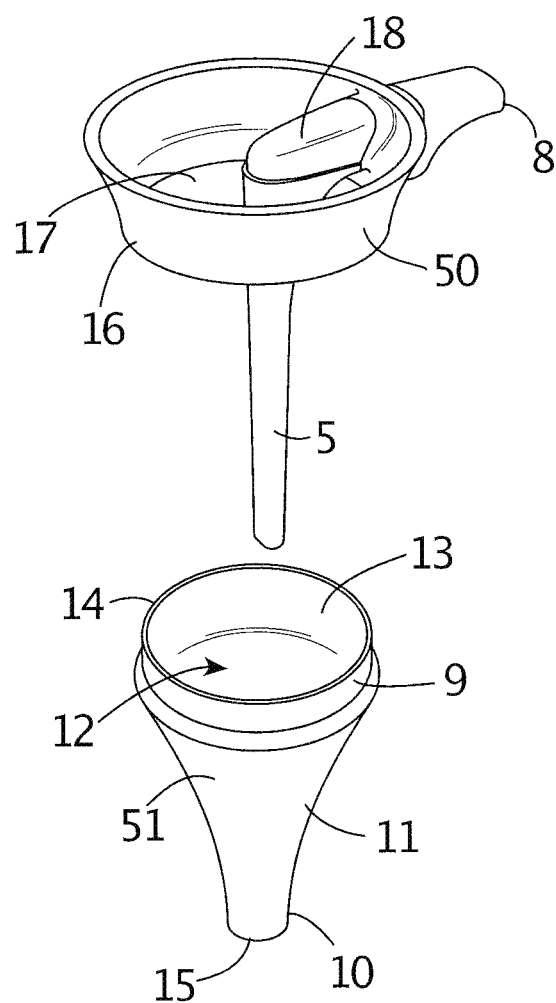
FIG. 3 is a partially exploded view from above and one side of the endoscope with the probe and endoscope handle of the stabilizer removed from the speculum.

As shown in FIGS. 1 to 3 of the accompanying drawings, a first embodiment of a scope of the invention is generally indicated by the reference numeral 1 and has a stabilizer 2 made up of a speculum holder 50 and a speculum 51 attached to the speculum holder 50. The speculum holder 50 can be in the form of a speculum handle 3 defining a collar 4 for receiving and holding the speculum 51. The scope 1 also has a flexible or rigid integrated elongate probe 5 attached to the collar 4 and located in the speculum 51. The probe 5 is fitted with at least one camera 6 and a light source 7 for visualising the ear and is preferably formed from materials that allow the probe 5 to have a low mass. A data cable 8 extends from the probe 5 via the collar 4 to a display (not shown) to display images from the camera 6.

The stabilizer 2 is configured to stabilize the device in an ear canal in use. More particularly, as the probe 5 is integrated with the stabilizer 2 in a unitary scope and stabilizer structure, a combined or unified speculum-probe scope assembly results in which the stabilizer 2 supports the probe 5 in or on the stabilizer 2 in use to allow for two handed surgical techniques. In one embodiment, the probe 5 and/or the camera 6 and the stabilizer 2 can be separate entities i.e. the probe 5 and/or the camera 6 can be mountable on the stabilizer 2. However, in this embodiment, when mounted on the stabilizer 2, the probe 5 and/or the stabilizer 2 define the integral or unified stabilizer 2—probe 5/camera 6 configuration. The assembly can be in the form of an otoscope for examining ears or a surgical endoscope which allows for bi-manual diagnosis and surgical techniques whilst benefiting from the advantages associated with endoscopic visualisation of the ear.

For the purposes of the following description, the scope 1 will be described principally in relation to its use as a surgical endoscope unless otherwise indicated.

The speculum 51 is made up of a proximal open end 9 through which a surgeon can access an ear during surgical procedures and a distal insertion end 10 insertable in an ear. In surgical applications, the speculum 51 serves as a working channel approximating a conical shape, which also serves to accommodate the probe 5 as well as surgical tools placed in the working channel. A substantially conical speculum wall 11 extends between the proximal and distal ends 9,10 which defines an internal chamber 12 for receiving the probe 5 and surgical instruments in use. The conical speculum wall 11 further defines a relatively large surgical access opening 13 at a rim 14 at the proximal end 9 and a relatively narrow insertion opening 15 at the distal end through which a surgeon can access the ear during surgical procedures.

The collar 4 of the handle 3 has speculum mounting in the form of a ring 16 defining a bore 17 for receiving the rim 14 of the speculum to mount and secure the handle 3 to the rim 14 of the speculum 51. The collar 4 is further provided with a probe mounting 18 to mount the probe 5 on the handle so that the elongate probe 5 can extend through the speculum 51 from the proximal end 9 to the distal end 10 and exit the distal end 10 through the insertion opening 15 if required.

The scope 1 is configured or weight balanced to maintain its centre of gravity within the volume contained within the stabilizer 2 and the speculum 51 i.e. to maintain a low stabilising centre of gravity in use. This can be achieved in a number of ways by configuring or weight balancing the stabilizer 2 or speculum 51 to provide a weight balanced scope e.g. through the use of combinations of low density and high density materials in the construction of the scope 1 where the weight is increased below the speculum's 51 centre of gravity i.e. towards its distal end 10. For example, the scope 1 of the invention can be made up of a low density material (e.g. a polymer) at a portion towards the proximal end 9 of the speculum 51 and a portion towards the distal end 10 of the speculum 51 can be made from a high density material such as a metal material. Accordingly, the centre of gravity when placed in the ear of a patient lying on a surgical table with their ear pointing upwards is lowered. Furthermore, the use of metal in the speculum 51 towards the distal end 10 and at the insertion opening 15 is also advantageous as it allows lasers to be used without melting.

The speculum 51 can also be configured or weight balanced to maintain a low centre of gravity through the use of weights or balancing arms as discussed further below in relation to FIGS. 22 and 23.

Figure 4:
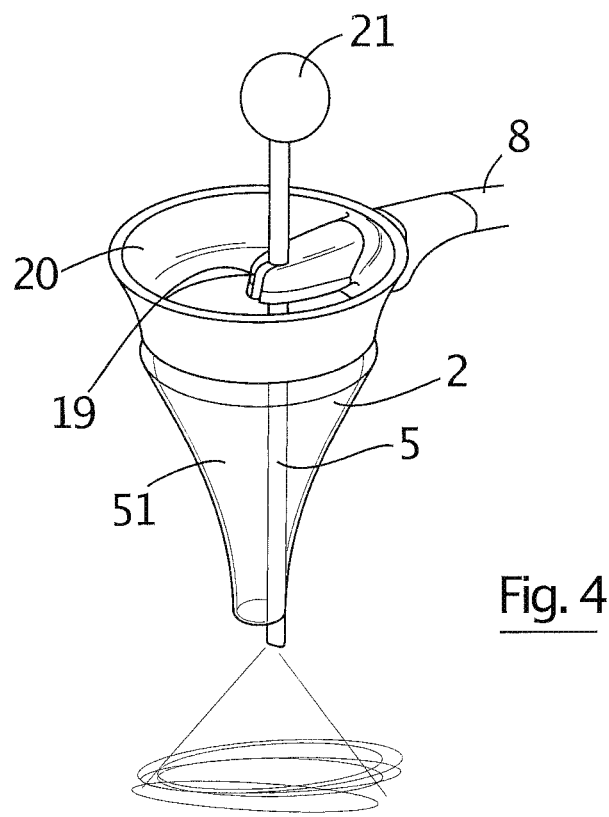
FIG. 4 is a perspective view from above and one side of a second embodiment of the endoscope in which the probe is slidably mounted on the speculum via a sliding mechanism and sliding movement of the probe is controllable via a sliding control knob.

FIG. 4 shows a perspective view from above and one side of a second embodiment of the scope 1 similar to the scope 1 of FIGS. 1 to 3 but in which the elongate probe 5 is slidably mounted on the speculum 51. Like numerals indicate like parts. More particularly, the elongate probe 5 is slidably mounted on the collar 4 at a probe moving mechanism 19. The probe moving mechanism 19 an encompass any suitable form of movement which allows for movement of the probe 5 e.g. proximal or distal movement of the probe 5. In the present embodiment, the probe moving mechanism 19 is a probe sliding or translating mechanism 19 so that the elongate probe 5 can be slidably inserted through and slidably removed from the speculum 2 as required. Accordingly, the elongate probe 5 can slidably project from the narrow insertion opening 15 as required in use to facilitate enhanced visualisation of the ear as shown in the drawing.

In the present embodiment, the sliding mechanism 19 is in the form of friction fit/mounting slot 20 defined in the probe mounting 18 for slidably receiving the elongate probe 5. Sliding movement of the probe 5 in the sliding mechanism 19 is controllable via a manually operable probe depth control actuator mechanism 21 in the form of a sliding control knob 21 attached to the elongate probe 5 to control the depth of insertion of the probe 5. The mechanism 21 can be provided with a stop to prevent over insertion which, in some embodiments, can be overridden with an override button, e.g. a clickable button, if desired.

The probe sliding mechanism 19 is typically in the form of a friction fit/mounting, and preferably a low friction fit/mounting, defined between the stabilizer 2, and in particular the collar 4 of the speculum holder 50, and the probe 5. A low friction fit/mounting is possible where the probe 5 has a low mass so that a user can dynamically adjust the probe 5 without the need to lock, unlock or actuate a mechanism per se i.e. the low friction holds the probe 5 in place whilst also allowing sliding movement of the probe 5. The probe is therefore moveable by direct interaction to overcome friction and, when released, regains its stationary position once again. In this embodiment, the sliding mechanism 19 effectively enables frictional holding of the probe 5 as opposed to strict movement of the probe 5.

Figure 5:
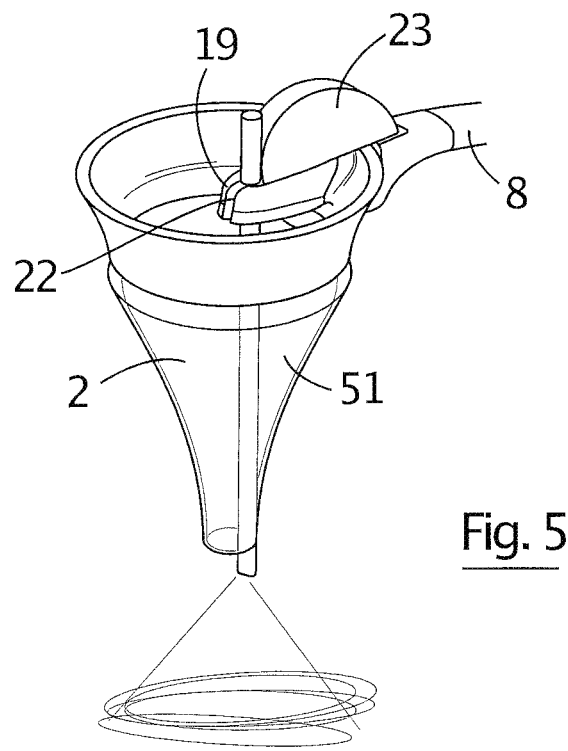
FIG. 5 is a perspective view from above and one side of the endoscope of FIG. 4 in which sliding movement of the probe is controllable via a control wheel.

FIG. 5 shows a perspective view from above and one side of the scope 1 of FIG. 4 in which the sliding mechanism 19 is provided with a mechanical coupling 22 to couple the elongate probe 5 to the probe mounting 18 and a manually rotatable control wheel 23 to effect sliding movement of the elongate probe 5 via the mechanical coupling 22.

Figure 6:
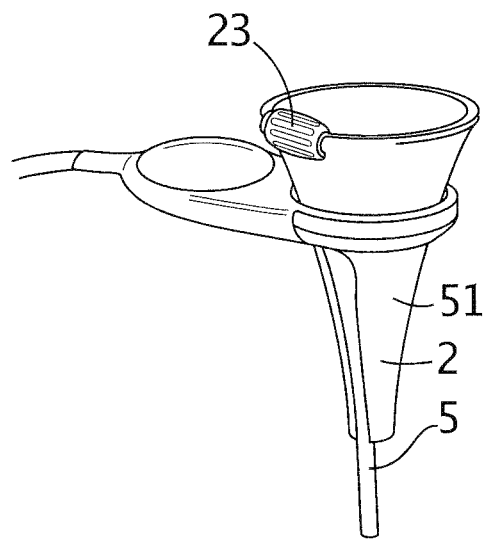
FIG. 6 is a perspective view from above and one side of the endoscope of FIG. 5 in which the control wheel has a flattened configuration.

FIG. 6 shows a perspective view from above and one side of the scope 1 of FIG. 5 in which the control wheel 23 has a flattened ergonomic configuration.

Figures 7, 8:
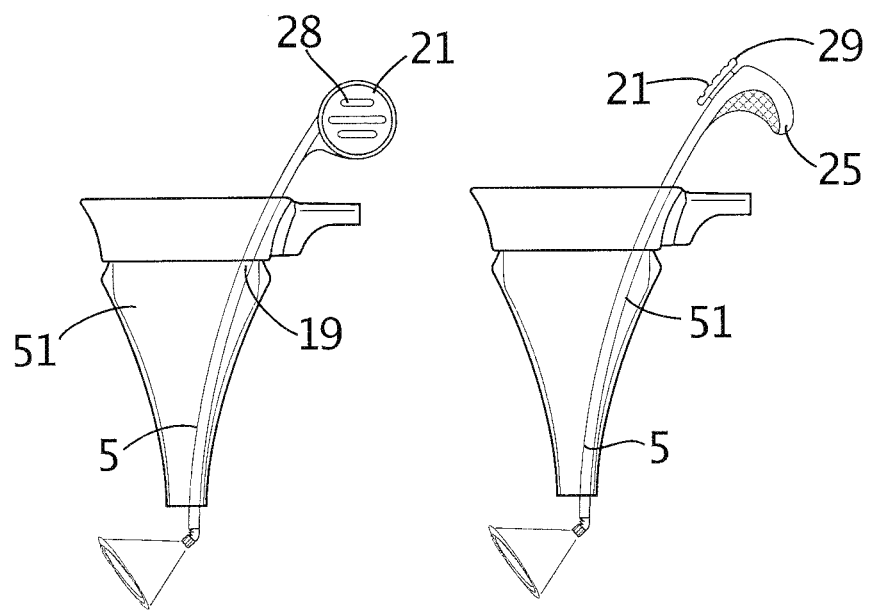
FIG. 7 is a side elevation of a third embodiment of the endoscope in which the probe is curved to conform with the speculum and provide free access space for a surgeon and the probe is slidable to adjust the depth of the probe.
FIG. 8 is a side elevation of the endoscope of FIG. 7 in which the depth of the probe camera is adjustable via a slider.

FIG. 7 is a side elevation of a third embodiment of the scope 1 in which, in addition to the elongate probe 5 being slidable, the elongate probe 5 is curved to conform with at least a portion of the contour of the wall 11 of the speculum 51 to create additional space in the speculum chamber 12 for a surgeon in use. The scope 1 is provided with a depth control actuator 21 in the form of a wheel 28.

FIG. 8 is a side elevation of the endoscope of FIG. 7 but in which the depth control actuator 21 is in the form of a slider 29 on a grip 25.

Figure 9:
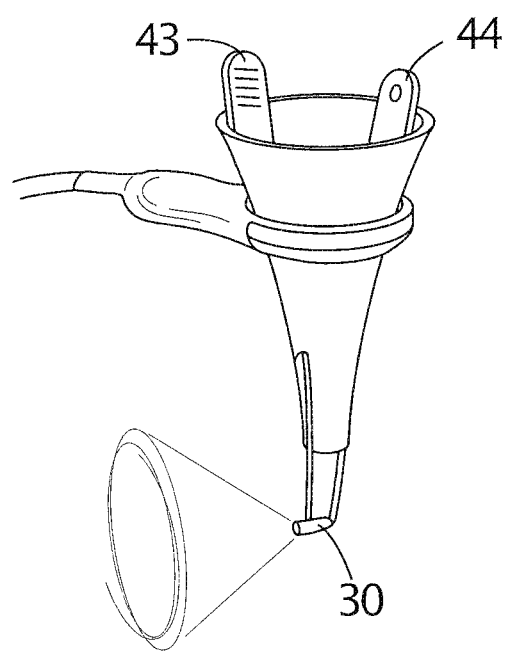
FIG. 9 is a perspective view from above and one side of a fourth embodiment of the invention in which the scope is provided with a pair of oppositely disposed probe support arms located either side of the speculum.

FIG. 9 shows a perspective view from above and one side of a fourth embodiment of the scope 1 of the invention similar to the embodiments previously described in which the scope 1 is provided with first and second oppositely disposed support arms 43, 44 respectively located either side of the speculum 2 and parallel with the speculum wall 11 to hold a cameral module 30 at the distal insertion end 10. The camera module 30 is disposed in a vertical position when the support arms 43, 44 are brought together.

Figure 10:
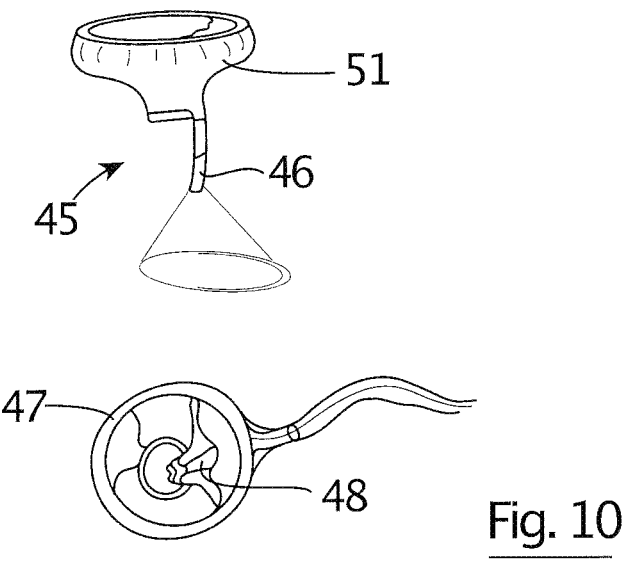
FIG. 10 is a side and top view of a fifth embodiment of the invention in which the scope is provided with a flexible section to allow flexible orientation of the probe and tool rest and guides for surgical tools.

FIG. 10 shows a side and top view of a fifth embodiment of the invention in which the wall 11 of the speculum 51 is provided with a flexible section 45 towards the distal insertion end 10 to allow flexible orientation and positioning of the elongate probe 5. The flexible section 45 is made up of an elongate flexible tube 46 for resiliently holding the elongate probe 5 in position. The speculum collar 4 is also provided with an instrument rest 47 and guides 48 for surgical instruments.

Figure 11:
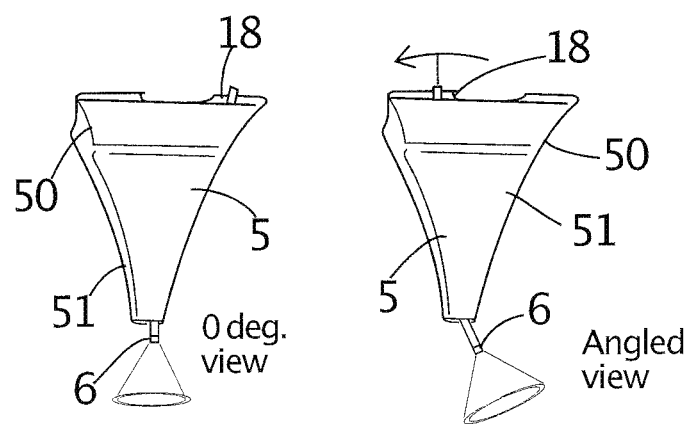
FIG. 11 is a side elevation of a sixth embodiment of the invention similar to the endoscope of FIG. 7 but in which the curved probe can be disposed against or adjacent the speculum wall as shown in FIG. 7 or spaced apart from the speculum wall and rotatably re-oriented to provide an angled camera view.

FIG. 11 shows side elevations of a sixth embodiment of the invention similar to the endoscope of FIG. 7 but in which the curved probe 5 is detachable so that the elongate probe 5 can be disposed against or adjacent the speculum wall 11 as shown in FIG. 7 or spaced apart from the speculum wall 11 and re-oriented to provide an angled camera view. More particularly, the curved probe 5 is rotatably mounted in the probe mounting 18 to change the angle of view of the camera 6 as required.

Figure 12:
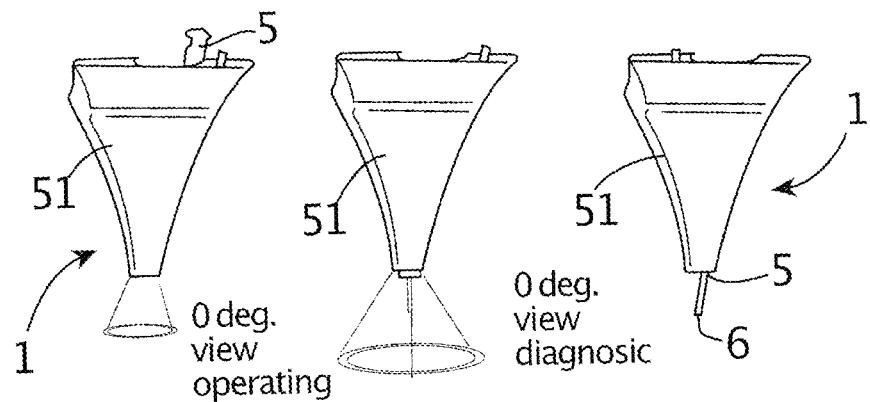
FIG. 12 is a side elevation of the seventh embodiment of the invention similar to the embodiment of FIG. 11 but in which the probe is also slidable as shown in FIG. 4 with respect to the speculum.

FIG. 12 shows side elevations of the sixth embodiment of the invention of FIG. 11 but in which the probe 5 is also slidable as previously described with respect to the speculum 51.

Figure 13:
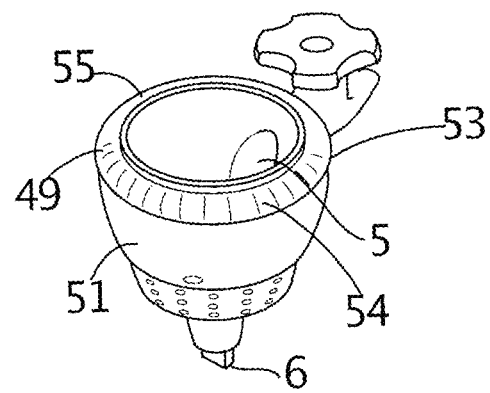
FIG. 13 is a side elevation of an eighth embodiment of the invention in which the scope is further provided with an image orienting mechanism to orient the image from the camera relative to the user as required.

FIG. 13 shows a side elevation of an eighth embodiment of the scope 1 similar to the scopes 1 previously described but in which the device 1 is further provided with an image orienting mechanism 49 to orient images from the camera 6 relative to the user as required. Like numerals indicate like parts. In the present embodiment, the image orienting mechanism 49 is made up of rotatable or rotational control 53 on the stabiliser 2, and more particularly on the proximal end 9 of the speculum 51, in the form of a peripheral rotatable ring or dial 54 rotatably mounted on the speculum 51 to be manually rotatable with respect to the speculum 51 and the camera 6. The image orienting mechanism 49, in combination with software, facilitates digital rotation and orientation of images from the camera 6 i.e. the images from the camera 6 can be oriented as required independent of the position of the probe 5. In the present embodiment, the dial 54 is provided with a directional guide or marker 55 to reference the orientation of the image e.g. to reference the vertical up direction. The dial 54 is configurable to control software to digitally rotate images on a screen while, in other embodiments, automatic methods for rotating the images can be provided such as gyroscopes or tilt switches built into the device of the invention.

Another embodiment would include a button on the endoscope to take a snapshot of the image through software. Another embodiment to this button would allow a long hold option to take a video of the camera feed through software.

Figure 14:
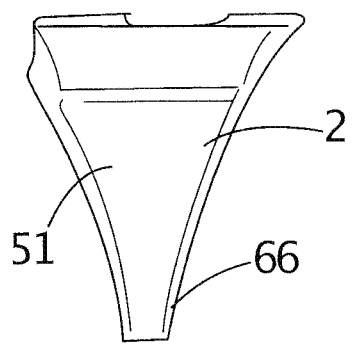
FIG. 14 is a side elevation of a ninth embodiment of the invention in which the speculum is provided with a lumen or channel for suction or for directing air or fluids into the ear as required.

FIG. 14 shows a side elevation of a ninth embodiment of the scope 1 of the invention in which the speculum 51 is further provided with an optional lumen or channel 66 for suction or for directing air or fluids into or towards the ear as required. The channel 66 can also serve to to clear lenses as required. If desired, the speculum 51 can be provided with two or more lumen or channels 66.

Figure 15:
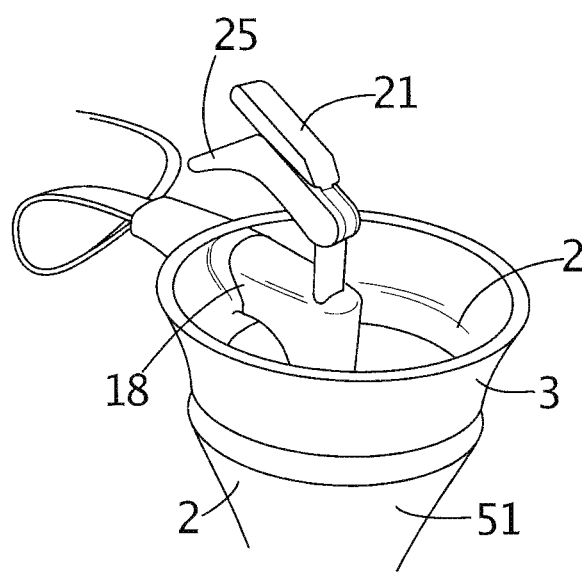
FIG. 15 is a perspective view from above and one side of a tenth embodiment of the invention in which the probe is slidable and orientable via a lever control.

FIG. 15 shows a tenth embodiment of the invention in which the probe 5 is slidable via a lever-like depth control actuators 21 as previously described.

FIGS. 16(a) to 16(c) show perspective views from above and one side of various speculum 51 types suitable for use with the scope 1 of the invention in which the speculum wall 11 can be continuous as shown in FIG. 16(a), provided with a simple cut or cutaway portion 68 as shown in FIG. 16(b) or a profiled cut or cutaway portion 68 as shown in FIG. 16(c). The cutaway portions 68 facilitate easy removal of instruments and access to the superior ear canal as required.

FIG. 17 shows a perspective view from above and one side of an eleventh embodiment of the invention in which the speculum 51 of the scope 1 of FIG. 16(b) is provided with two oppositely disposed cutaway portions 68 to define two oppositely disposed speculum blades 69 which can be expanded and contracted at the cutaway portions 68 via an expansion mechanism 70 disposed adjacent the probe mounting 18. In some embodiments, more than two cutaway portions 68 can be provided. The expansion mechanism 70 is controllable via a knob-like expansion mechanism actuator 71 to effect expansion and contraction of the blades 69. The expansion mechanism 70 has a right-handed screw thread acting on one blade 69 and a left-handed screw thread acting on the opposite blade 69 so that the two blades expand equal distances from the probe 5, and hence the camera 6, in use. The speculum blades 69 are kept in line with each other, by the relationship of the at least one guide pin 94 and the expansion mechanism 70.

Figure 18:
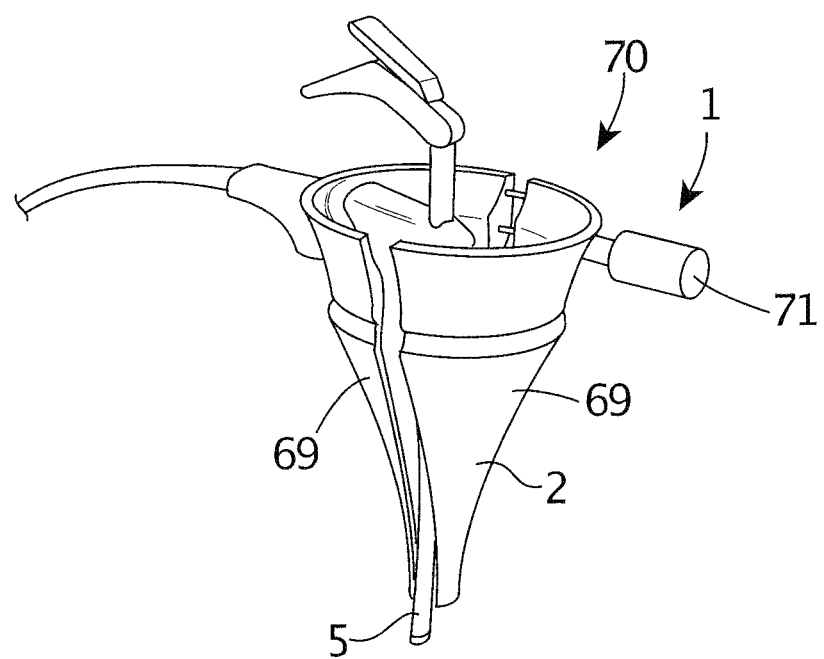
FIG. 18 is a perspective view from above and one side of a scope similar to the scope of FIG. 17 but in which the probe moves with one blade of the speculum during expansion and contraction.

FIG. 18 shows a perspective view from above and one side of the scope 1 similar to the device of FIG. 17 but in which the probe 5 moves with one blade 69 of the speculum 51 during expansion and contraction.

Figure 19:
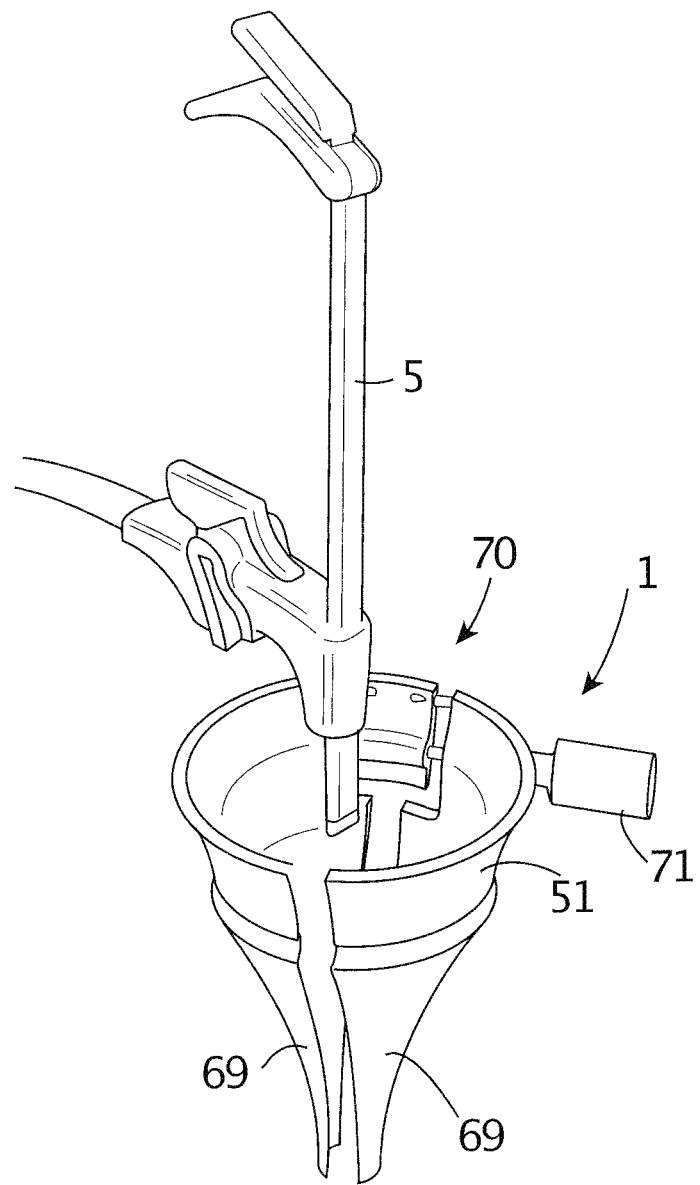
FIGS. 19 and 20 are perspective views from above and one side of the scope of FIG. 18 in which the probe can be lifted and positioned within the speculum as required by a user.
Figure 20:
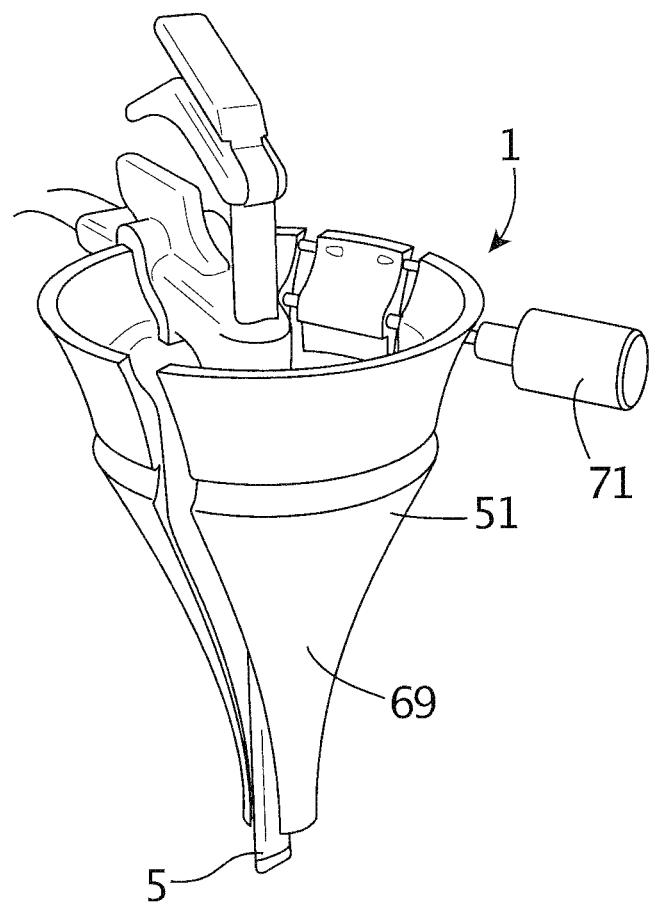

FIGS. 19 and 20 are perspective views from above and one side of the device of FIGS. 17 and 18 in which, in addition to the expansion mechanism 70, the scope 1 is provided with a probe 5 that can be lifted and positioned within the speculum 51 as required by a user as previously described.

Figure 21:
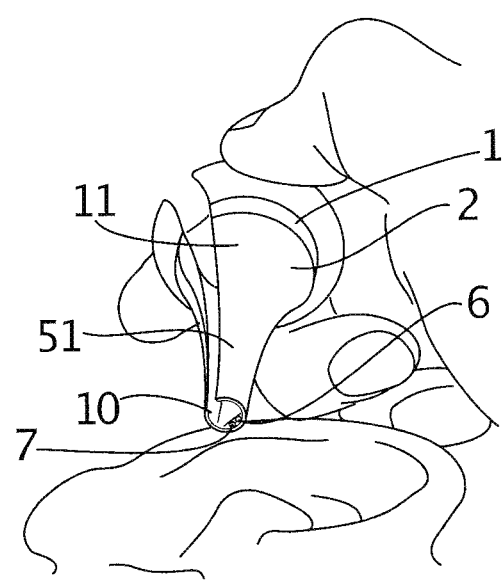
FIG. 21 is a perspective view from above and one side of a further embodiment of a scope of the invention similar to the scope of FIG. 16 but in which the camera and light source are built-in or integral with the wall of the speculum and the scope is held in a user's hand at a patient's ear.

FIG. 21 shows a perspective view from above and one side of a further embodiment of the scope 1 of the invention similar to the scope of FIG. 16 but in which the camera 6 and light source 7 are not in the form of a probe 5 per se but are built-in to the wall 11 of the stabilizer 2 and in particular the speculum 51. More particularly, the camera 6 and the light source are integral with and located in or on the wall 11 of the speculum 51 towards the distal insertion end 10 of the scope 1 so that the speculum 1, the camera 6 and the light source 7 are in the form of a unitary structure. Accordingly, a separate probe 5 can be dispensed with.

The cutaway portions 68 shown in FIGS. 16 to 21 define openings in the wall 11 of the speculum 51 to allow surgical tools and implements to be removed from the speculum 51, and hence the scope 1, through the openings defined by the cutaway portions 68 e.g. a large foreign body can be removed through a cutaway portion with a surgical tool such as a forceps which would not otherwise fit through the insertion opening 15.

Figure 22:
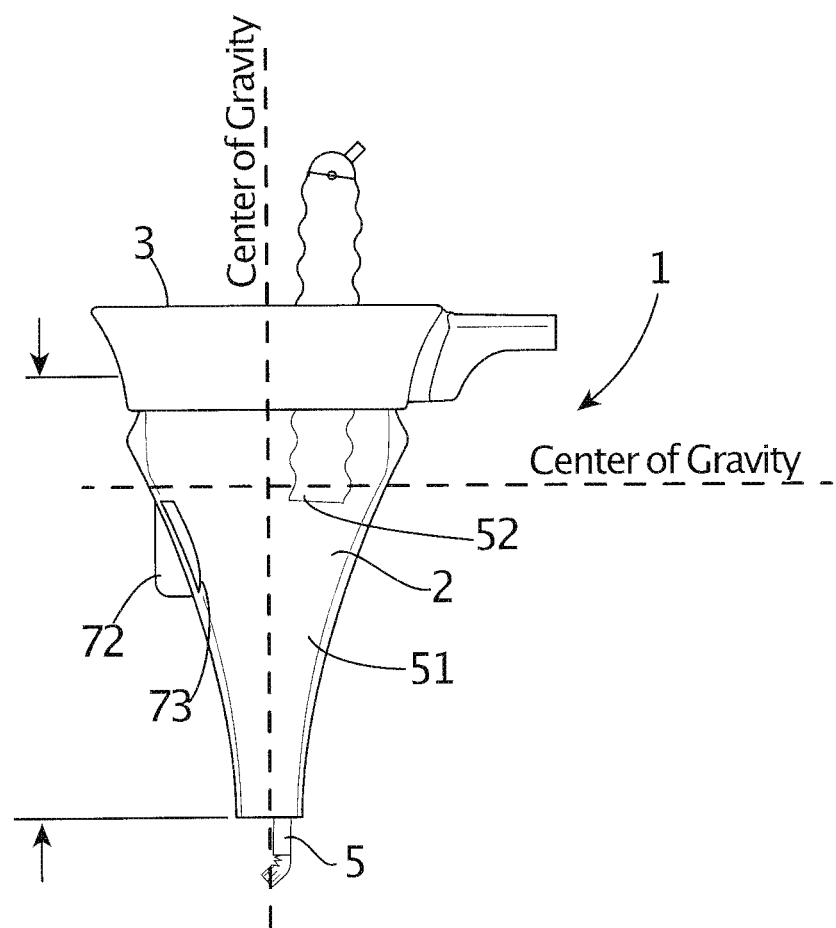
FIG. 22 is a side elevation of a further embodiment of the invention in which the scope is balanced with a balancing weight to ensure that the centre of gravity of the scope is within the volume contained within the speculum.

FIG. 22 is a side elevation of a further embodiment of the scope 1 of the invention broadly similar to device of FIGS. 1 to 21 and like numerals indicate like parts. In the present embodiment, the stabilizer 2 is configured to stabilize and balance the device in the ear canal by maintaining its centre of gravity 52 within the volume contained within the speculum 51. More particularly, the stabilizer is balanced with a balancing weight 72 to ensure that the centre of gravity of the scope 1 is within the volume contained within the speculum 2 to allow the device to balance in the ear canal. The balancing weight 72 is located on a balancing weight mounting 73 which is positioned on the exterior of the speculum wall 11 to lower and centre the centre of gravity of the scope 1.

In an alternative embodiment, the balancing weight 72 can be attached to and/or be integral with the probe 5.

Figure 23:
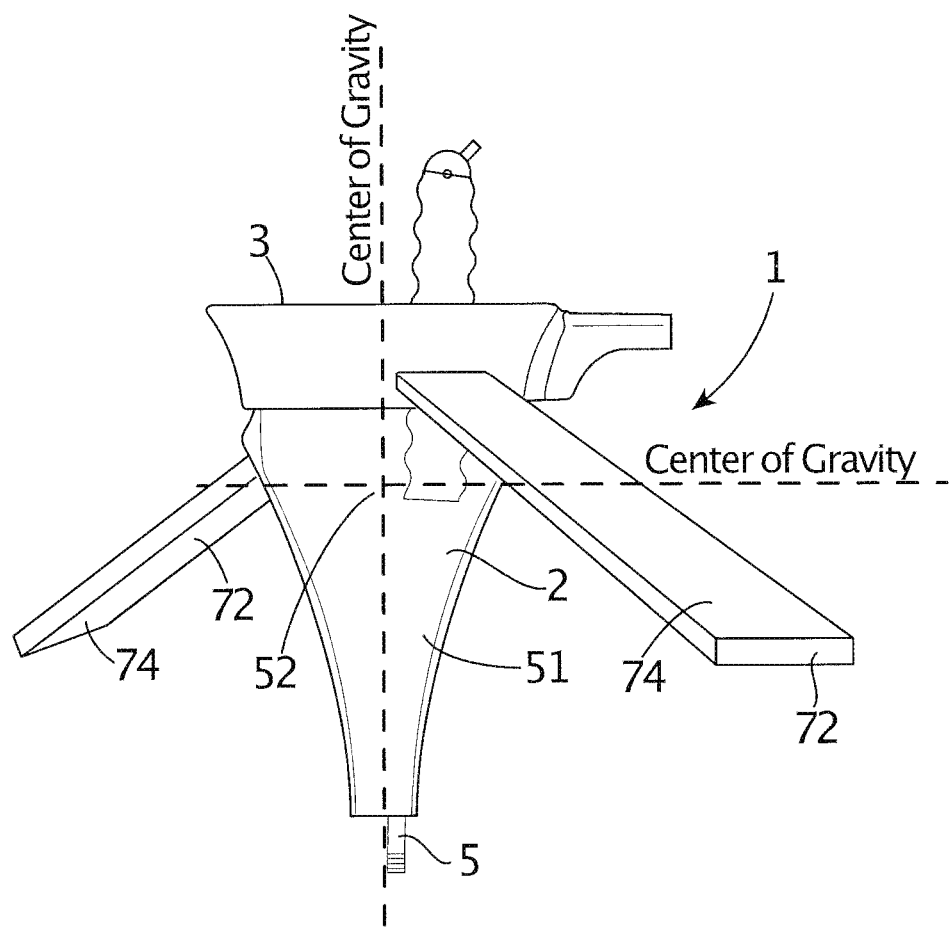
FIG. 23 is a side elevation of an alternative embodiment of the scope of FIG. 22 in which the balancing weight is in the form of balancing wings.

FIG. 23 is a side elevation of an alternative embodiment of the scope 1 of FIG. 22 in which the balancing weight 72 is in the form of two oppositely disposed balancing wings or arms 74 extending laterally outwards from the scope 1. In the present embodiment, a first balancing wing 74 extends laterally outwards from the collar 4 while the second balancing wing 74 extends laterally outwards from the speculum wall 11.

Figure 24:
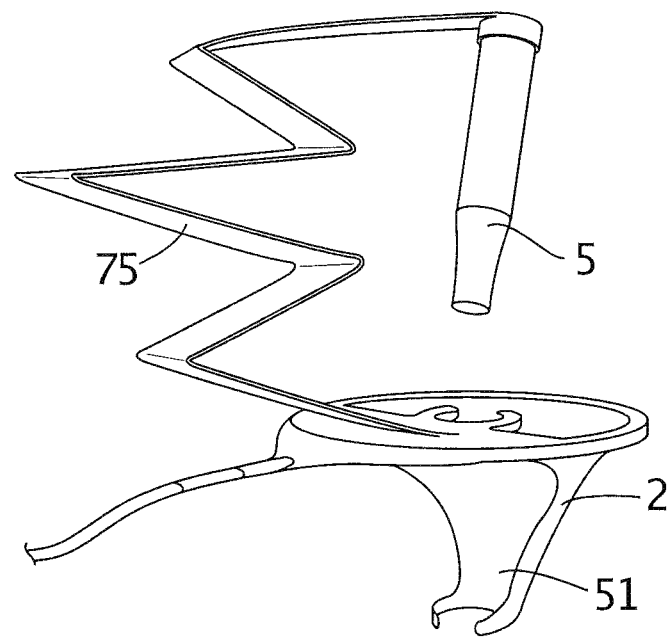
FIG. 24 is a perspective view from above and one side of an alternative embodiment of the invention in which the probe is detachable and removable from the speculum.

FIG. 24 shows a perspective view from above and one side of an alternative embodiment of the scope 1 of the invention in which the probe 5 is detachable and removable from the speculum 51 but is attached to the collar 4 of the speculum handle 3 via a wire 75. The probe 5 can therefore be used as a hyperbolic lens giving angled views as required.

Figure 25:
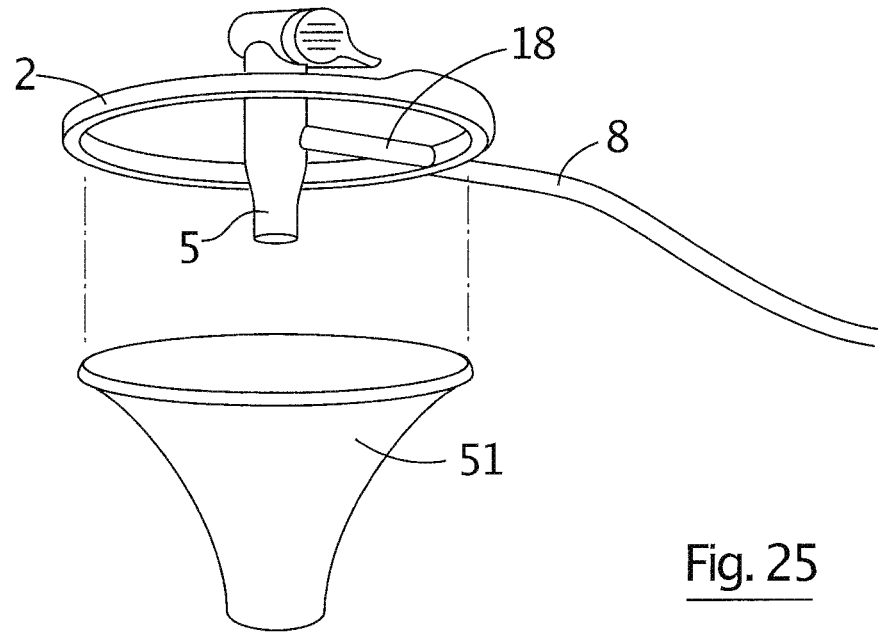
FIG. 25 is a perspective view from above and one side of an alternative embodiment of the invention in which a probe is provided with a speculum mounting so that the probe can be retrofitted to a conventional speculum.

FIG. 25 shows a perspective view from above and one side of an alternative retrofittable embodiment of the scope 1 of the invention in which the speculum 51 is omitted and a probe 5 is provided on a retrofittable speculum handle-like stabilizer 2 in the form of a speculum holder 3 which can be retrofitted to a conventional pre-existing speculum 51 by attaching the speculum holder 3 to the pre-existing speculum 51. The handle-like speculum holder 3 is similar to the speculum handle 3 previously described and is provided with a collar 4 and a flexible or rigid integrated elongate probe 5 attached to the collar 4 and locatable in a conventional known speculum 2 retrofitted with the speculum holder 3. The speculum holder 3 is provided with a ring 16 as previously described to receive a speculum 51 and a probe mounting 18 to support the elongate probe 5 in the speculum holder 3 and the speculum 51 in use.

Figure 26:
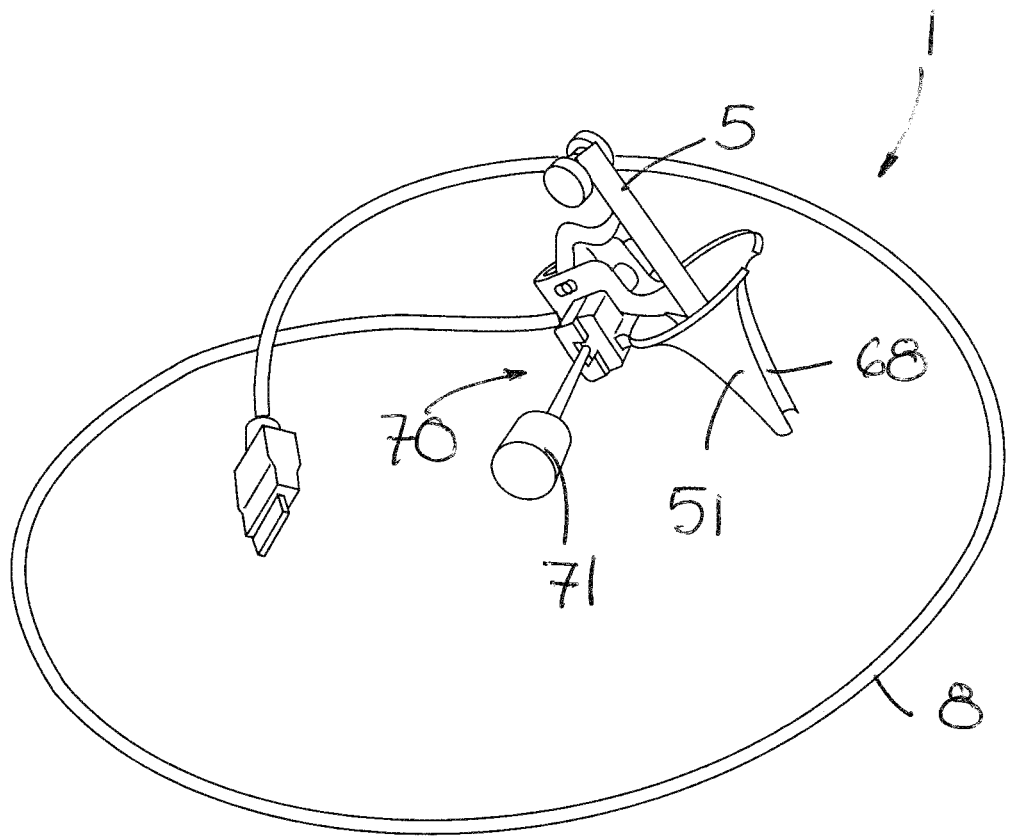
FIG. 26 is a perspective view from above and one side of a scope of the invention in which the speculum is provided with a cutaway portion controllable via an expansion mechanism with an expansion mechanism actuator.

FIG. 26 shows a perspective view from above and one side of a scope 1 of the invention similar to the scopes previously described in which the speculum 51 is provided with a cut or cutaway portion 68 controllable via an expansion mechanism 70. Like numerals indicate like parts. The expansion mechanism 70 can be actuated via an expansion mechanism actuator 71 to effect opening and closing of the opening defined by the cutaway portion 68. As shown in the drawing, a data cable 8 extends from the probe 5 to a display (not shown) to display images from the camera 6 on the probe 5.

In use, a user places the speculum 51 into the ear canal and adjusts the size of the speculum 51 (or chooses the correct speculum size as required). The user can clip/screw/glue/place/tape a scope holder (discussed further below) onto the patient's head/ear, or patient bed, or patient pillow, or patient covers. Where the holder 76 is deformable, the user can bend the speculum holder to shape and it will maintain that shape until bent again.

Accordingly, the user has the ability to balance the speculum 51 in the canal and use both hands for tools for example suction and curette to perform the surgery. The user can look at a screen to see the camera feed and can take pictures and videos of the camera feed whilst zooming in and out the camera image as required. If desired, the user can wear 3D glasses to allow for depth perception of the camera.

As indicated above, the user can slide the probe up and down to adjust focus as required and can also set a depth control mechanism that may be either pre-set or can be adjustable to set which will stop the probe from moving as the surgeon is performing the surgery. If the user wants to go past this, they will unlock it and further extend the probe.

The user can move the probe along the horizontal plane to move both operating tools to one side of the camera as required and can change the orientation of images through a mechanical movement, if required.

A user can also clean the camera lens while the speculum is still in place by pulling the probe up, by applying suction through the lumen 26, by irrigating the camera and/or twisting the camera, by wiping the lens with a wipe inbuilt into the probe.

The user can also remove the speculum 51, clean the scope, reposition the speculum 51 and continue the procedure as required.

More specifically, in use, the scope 1 of the invention as described in FIGS. 1 to 26 in which the scope 1 of the invention is made up of a unitary stabilizer 2 and elongate probe 5 or a stabilizer/speculum 2 with a built-in camera 6 and light source 7 in which a pre-existing conventional speculum 51 is retrofitted with a scope 1, is positioned in a patient's ear for surgery and, optionally, supported in place with a scope holder (discussed further below).

As indicated above, the scope 1 is weight balanced to maintain its centre of gravity within the volume contained within the speculum 51 i.e. to maintain a low stabilising centre of gravity in use. More particularly, the speculum 51 has an increased weight below its centre of gravity i.e. towards its distal end. Accordingly, the scope 1 is stabilised in an ear canal in use to allow for bi-manual diagnosis and surgical techniques whilst benefiting from the advantages associated with endoscopic visualisation of the ear. Moreover, the cutaway portions 68 allow surgical tools and implements to be removed from the speculum 51 during surgery.

During surgery, the speculum 51 can be positioned as required relative to the ear and the probe 5 can in turn be moved as required relative to the speculum 51, with or without a scope holder. In particular, without a scope holder, a dynamic two handed technique can be used by a surgeon, while holding two surgical tools at the same time, for example a suction and a curette, with a surgeon's finger or fingers or the tools also supporting the weight balanced and stabilised scope. As indicated above, this is made possible by the low centre of gravity of the scope 1 which makes it easy to balance. This is further enhanced by the low mass of the scope 1.

As indicated above, a sliding mechanism 19 in the form of a low friction sliding mechanism facilitates easy positioning of the probe 5 so that the probe 5 can be dynamically repositioned in use with ease. The sliding mechanism 19 can also allow tilting of the probe 5 so that space is provided to allow tools to be placed along one or the other side of the speculum 51.

In one embodiment, a scope holder can be employed with the scope 1 of the invention. For example, the scope 1 can be equipped with a proprietary spigot which protrudes from the scope 1 and interfaces with the scope holder. The scope holder can be detached from the device via the spigot to aid autoclaving. Suitable scope holders within the scope of the invention are described further below in FIG. 27 and in particular FIG. 28

During surgery, typically, the scope holder is provided with a plate that rests in front of the ear on a surgical drape and is clipped to the drape using surgical forceps or a built-in clip which can be provided on the scope holder. This clip can have any suitable tightening mechanism such as a simple screw tightening, ratchet, spring or elasticated tightening mechanism.

Figure 27A:
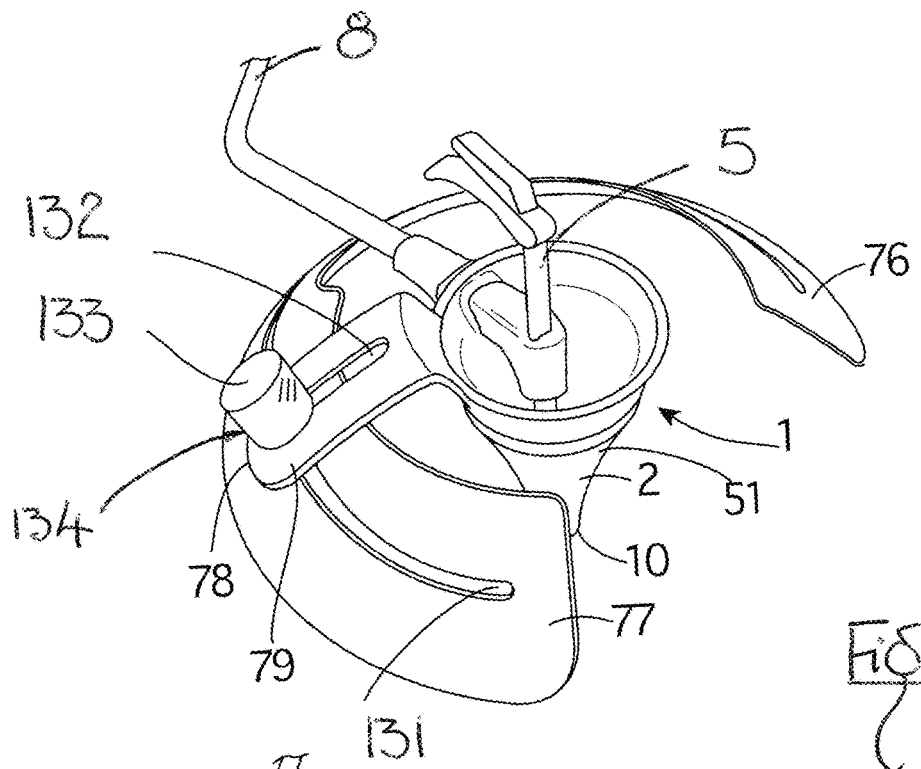
FIG. 27(a) is a perspective view from above and one side a scope system of the invention made up of a scope and a scope holder provided with a part-spherical (e.g. hemispherical) mounting plate for aligning the scope in use
Figure 27B:
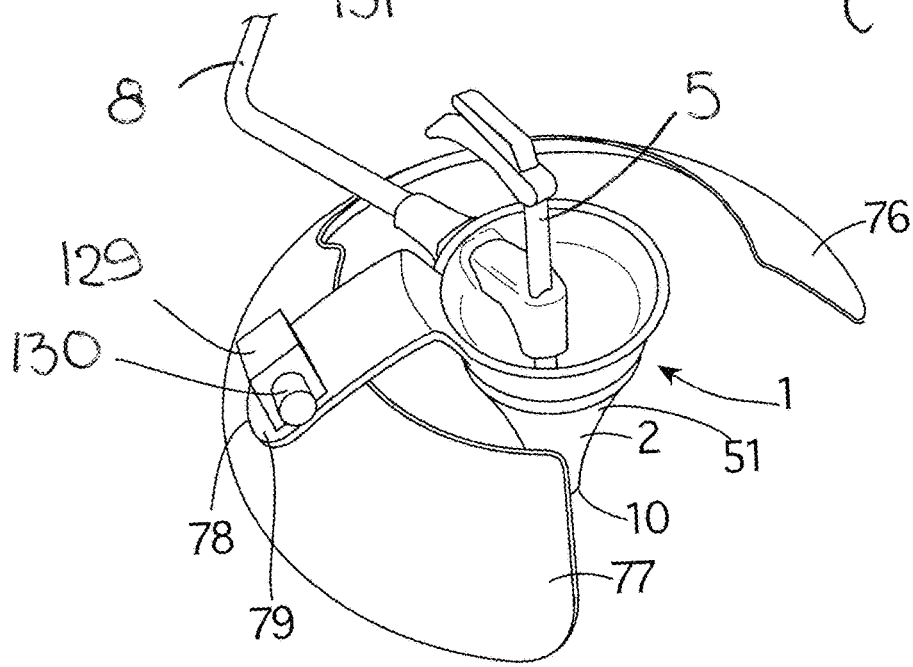
FIG. 27(b) is a perspective view from above and one side the scope system in which the scope system is adjustable at a slot in the part-spherical mounting plate.

As indicated above, the scope 1 of the invention can be used with a scope holder if desired. FIGS. 27(*a*) and 27(*b*) show perspective views from above and one side a scope system of the invention made up of a scope 1 and a scope holder 76 provided with a part-spherical mounting and positioning plate 77 for aligning the scope 1 in use. More particularly, the part-spherical mounting plate 77 is positioned with respect to the scope 1 so that the speculum 51 is centered within the notional circle defined by the part-spherical mounting plate 77 i.e. the speculum 51 is centrally located within the part-spherical mounting plate 77 so that the centre point of the part-spherical sphere defined by the mounting pate 77 aligns with the distal insertion end 10 of the speculum at 51. Due to the centering of the speculum within the part-spherical mounting plate 77, a surgeon can easily realign the device of the invention in one movement in a way that would not be possible with articulated arms or the like. In the present embodiment, light can also be transmitted through the structure of the scope 1 e.g. through the speculum 51 to the probe camera 6.

The part-spherical mounting plate 77 is attached to the speculum 51 via one or more wing-like arms 78. In the present embodiment, one arm 78 extends between the peripheral part-spherical mounting plate 77 and the speculum 51. The arm 78 is shaped and contoured to match the spherical shape and contouring of the part-spherical mounting plate 77. The scope 1 is aligned with the mounting plate at a fastening 79 defined between the arm 78 and the mounting plate 77. A single fastening at 79 is sufficient to keep the scope 1 aligned to the mounting plate 77. In one embodiment shown in FIG. 27(*b*), the fastening at 79 is magnetic, preferably a double pole magnetic fastener 129, in this embodiment a control 130 is actuated to engage or release the magnet. In another embodiment, the fastening at 79 can include a first slot 131 along the mounting plate 77 and a second slot 132 on the arm 78 overlapping the first slot 131. A connecting pin 133 is positioned through both slots 131,132 to allow full range of movement between the scope 1 and the mounting plate 77, while maintaining the distal insertion end 10 of the scope 1 in place. The pin 133 is acted upon to clamp the mounting plate and arm together and is tightened using a hand nut or cam 134.

In one embodiment, the part-spherical mounting plate can be hemi-spherical.

In one embodiment, the scope holder 76 can be secured to a patient with adhesive or strapped to a patient.

The mounting plate 77 can be attached to a surgical drape as previously described or to a headrest mount described in more detail below.

FIGS. 28 and 29 show a perspective view from above and one side of an alternative scope holder 76 for holding a scope 1 in use. Like numerals indicate like parts. In the present embodiment, the scope holder 76 is a deformable scope holder 76 having a plasticity which allows reversible deformation of the scope holder 76. As shown in the drawings, in the present embodiment, the scope holder 76 is integral or combined with the data cable 8, which extends through the scope holder 76, to form a scope holder cum data cable 92 for simultaneously holding the scope 1 in place during surgery and transmitting data from the probe 5. The scope holder cum data cable 92 can be formed from any suitable material that is sufficiently deformable to allow dynamic positioning and re-positioning of the scope 1 so that the scope holder cum data cable 92 is in effect a dynamic scope holder 76. The low mass of the scope 1 combined with the low centre of gravity makes the integration of the scope holder 76 and the data cable 8 possible and any materials having a suitable plasticity can be employed for the scope holder cum data cable 92 e.g. materials having a deformable plasticity (e.g. as shown in the drawings elongate steel wires 93 or similar) with a low enough force as to be easily deformed (bent) but yet of sufficient strength to resist the weight of the scope 1.

The scope 1 of the present embodiment is also provided with a guide rail 135 which maintains the speculum blades in alignment with each other.

Accordingly, as shown in the drawings, the scope holder cum data cable 92 can therefore be attached to a patient's head 81 to hold the scope 1 in place during surgery.

In an alternative embodiment shown in FIG. 30, the deformable scope holder 76 of FIGS. 28 and 29 can be separate to and independent of the data cable 8. In this embodiment, the deformable scope holder 76 can be connected to the scope 1 e.g. to the speculum 51, over, adjacent or remote from the data cable 8.

An advantage of the scope holders 76 of the invention is that surgery need not be interrupted to make adjustments to either the probe 5 or scope 1 as they can be moved freely as required on the scope holders 76. Moreover, there is no heavy endoscope to hold which can tire out surgeons where procedures can be up to 4 hours long.

Figure 31:
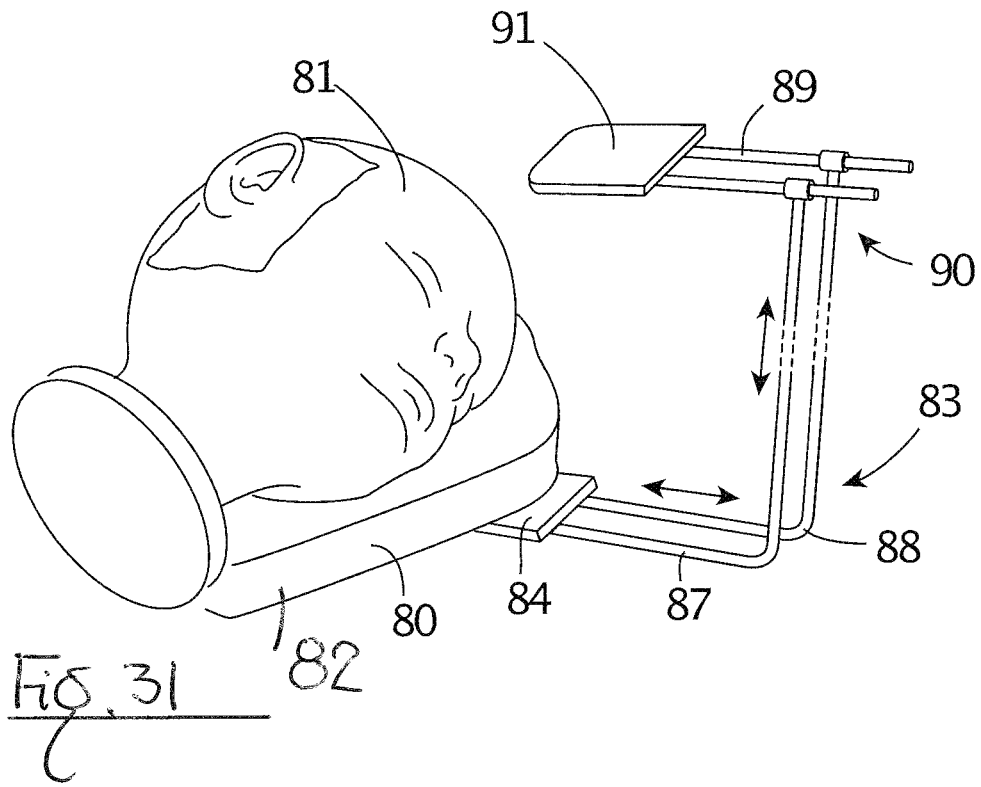
FIG. 31 is a perspective view from above and one side of an alternative scope system of the invention in which a headrest for supporting a patient's head is co-operable with a scope stand so that the stand self-adjusts in accordance with patient head movements with the scope holder of the scope stand being located away from a patient's ear.
Figure 32:
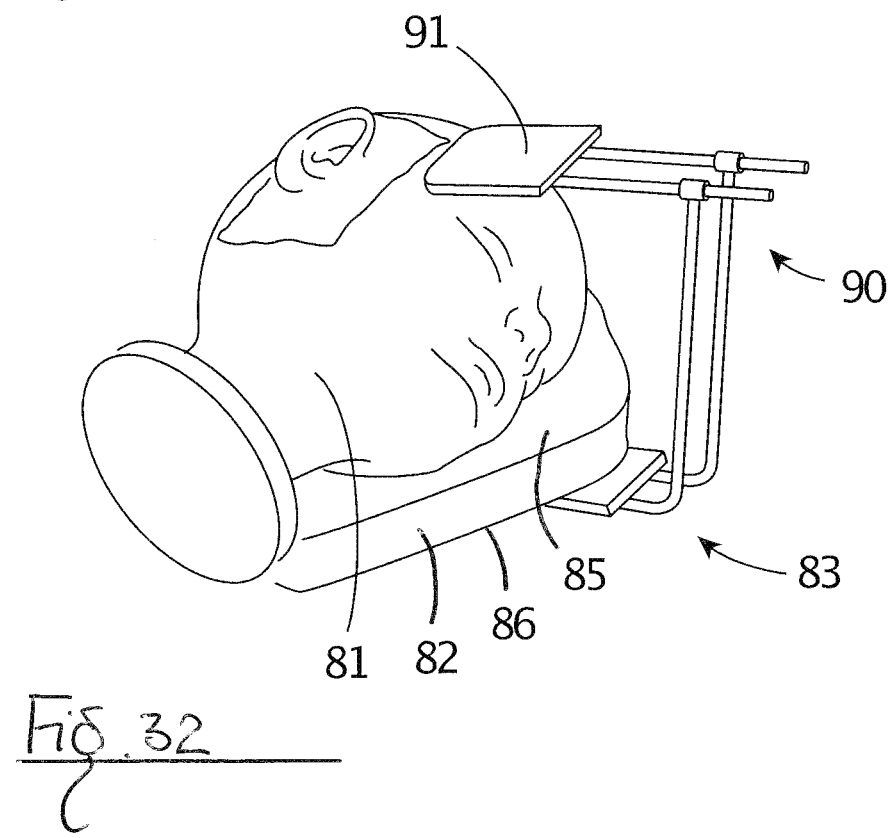
FIG. 32 is a perspective view from above and one side of the system of FIG. 31 with the scope holder being positioned adjacent a patient's ear.

FIGS. 31 and 32 show perspective views from above and one side of an alternative scope system of the invention in which a headrest device 80 for supporting a patient's head 81 self-adjusts in accordance with patient head movements. The headrest device 80 is made up of a headrest 82 and a scope stand 83 co-operable with the headrest 82 to move in response to headrest 82 movements to automatically re-position a scope 1 held in the scope stand 83. Although not shown in the drawings, the scope stand 83 can be adapted for use with the scope holder 76 of FIGS. 28 to 30.

As shown in the drawings, the headrest 82 is deployed under the patient's head 81. The upper face of the headrest 82 has a flat surface and is covered with a cushioning material 85 for the patient's head 81. The lower face of the headrest 82 has a convex shaped surface 86 which allows the headrest 82 to follow the patient's head movements. An articulated arm 87 extends from the headrest 82 to the stand 83. More particularly, the articulated arm 87 extends between the headrest 82 and a stand upright 88 which is in turn provided with an upper articulated arm 89 which projects from the upright towards the headrest 82 and the patient's head 81 to a location in front of the ear. The upper articulation arm 89 is made up of sliding and tilting sections 90 which can be locked rigidly in place. At its free end, the upper articulation arm 89 is provided with a scope mounting plate 91 to which a flexible arm can be mounted through the drape using a magnetic or mechanical fixing or the like without breaching the drape. The flexible arm can be attached directly to the scope 1 of the invention or to the scope holder of FIG. 33.

The headrest device 80 therefore removes the potential for surgical drapes to slip or move during surgery whilst also allowing the device to move relative to a patient's head and ear canal.

Figure 33:
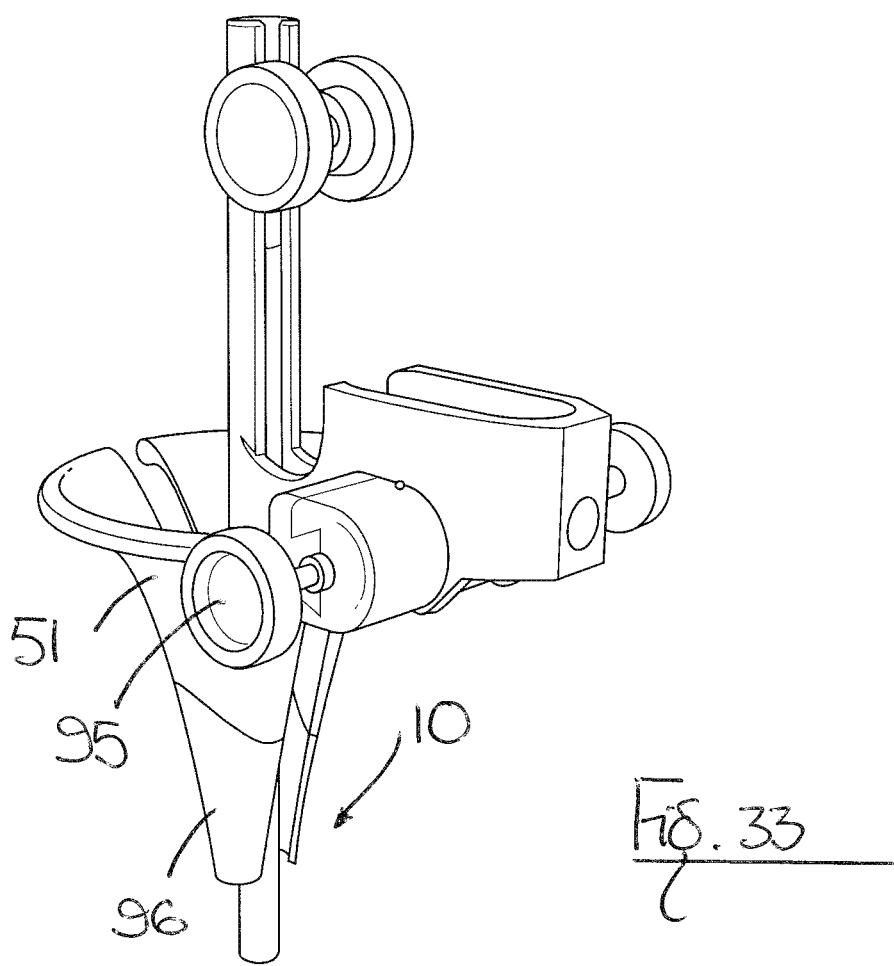
FIG. 33 is a perspective view from above and one side of a scope of the invention similar to the scope of FIGS. 28 to 30 with the holder omitted for clarity but in which the speculum is provided with a high density tip to weight balance the speculum.
Figures 40, 41:
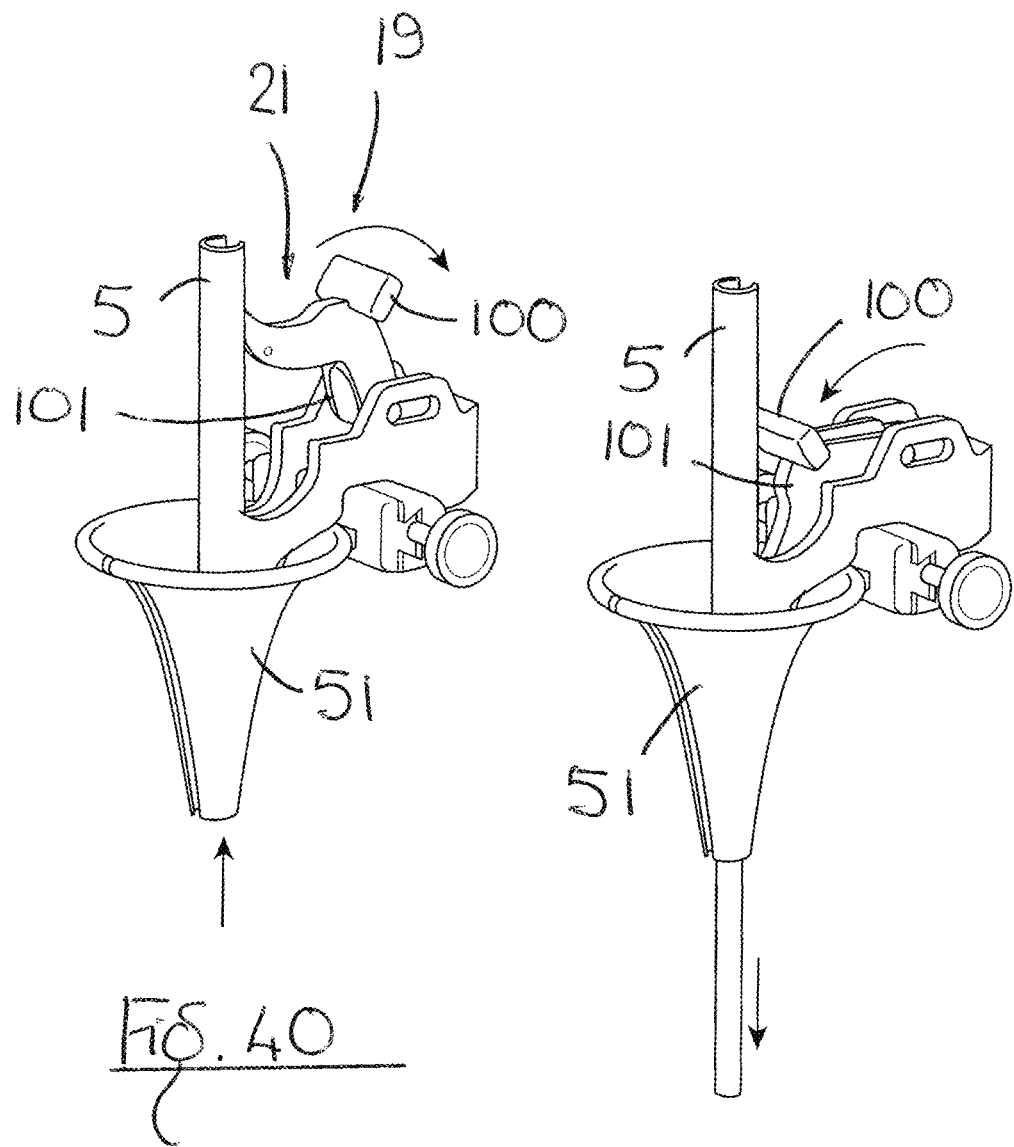
FIG. 40 is perspective view from above and one side of a further embodiment of the invention in which a probe depth control actuator mechanism gives haptic feedback to a user with the probe in a retracted position.
FIG. 41 is an alternate perspective view of the scope of FIG. 40 with the probe in an extended operating position.

FIG. 33 shows a perspective view from above and one side of a scope 1 of the invention similar to the scope of FIGS. 28 to 30 but with the holder 76 omitted and like numerals indicate like parts. However, in the present embodiment, the distal end 10 of the speculum 51 is provided with a high density tip 96 to weight balance the speculum 51.

FIGS. 34 to 37 show a perspective view from above and one side of an alternative embodiment of the scope 1 of the invention in which the speculum 51 is provided with four speculum blades 69 which can be expanded and contracted at cut portions 68 via an expansion mechanism 70 in the form of an adjustment ring 70 on the speculum 51 towards its proximal open end 9. Like numerals indicate like parts. The adjustment ring 97 is configured to define variable graduations 98 such as adjustment steps corresponding with different speculum sizes traditionally used in ear surgery, which can be selected in accordance with a user's experience i.e. the speculum blades 69 can splay out to enlarge the ear canal and can be sizably controlled by the rotatable adjustment 97 to bring the graduated steps 98 into contact with the blades 69 thereby pushing them out.

In an alternative embodiment of the invention, the expansion mechanism 70 can be in the form of a screw thread to bring a tube into contact with the blades 69 thus giving full analogue control of blade opening and closing.

As will be appreciated by those skilled in the art, the blades 69 may be molded in one part or be separate components.

FIGS. 38 and 39 show an alternative embodiment similar to the embodiment of FIGS. 34 to 37 but in which the expansion mechanism 70 is in the form of a band of resilient material 99 such as an elastomer over the speculum blades 69 with the blades 69 in a contracted or closed position and an open position respectively. Like numerals indicate like parts. The resilient band 99 is disposed towards the open distal end 10 of the speculum 51 and is positioned over the speculum 51 to cover the cuts 68 between the blades 69 and acts on the blades 69 to pull them back to a closed position as required.

FIGS. 40 to 44 show a further embodiment of the invention similar to the embodiments previously described but in which the probe depth control actuator mechanism 21 of the low friction probe sliding mechanism 19 is configured to give haptic feedback to a user. The haptic feedback can be provided by way of a wheel or cog 100 in contact with the probe 5 as shown in FIG. 42. As shown in FIG. 43, the wheel 100 is in communication with the probe 5 under the force of a spring 101 and optionally the wheel 100 has internal gear teeth 102 indexing with a pawl 136 so that when the gear teeth 102 overcome the pawl 136 feedback is given in the form of feel and/or a clicking sound i.e. the pawl 132 acts on the internal cog 102 to provide haptic feedback as described above. Optionally, the probe 5 may have a rack gear and a spring 101 may be used to maintain the contact force. Accordingly, in use, a surgeon can feel how deep the probe 5 is being pushed with haptic feedback e.g. in the form of clicks. As shown in FIG. 44, the probe sliding mechanism 19 gives haptic feedback to a user via a pawl and ratchet 137 directly in contact with the probe 5.

In another embodiment a sensor (not shown) could be deployed directly on the probe 5 or on the cog 100 or wheel 103. Data from this sensor would provide information on the relative movement between the prob 5 and the distal insertion end 10. This information could be displayed on a display monitor.

Figure 45:
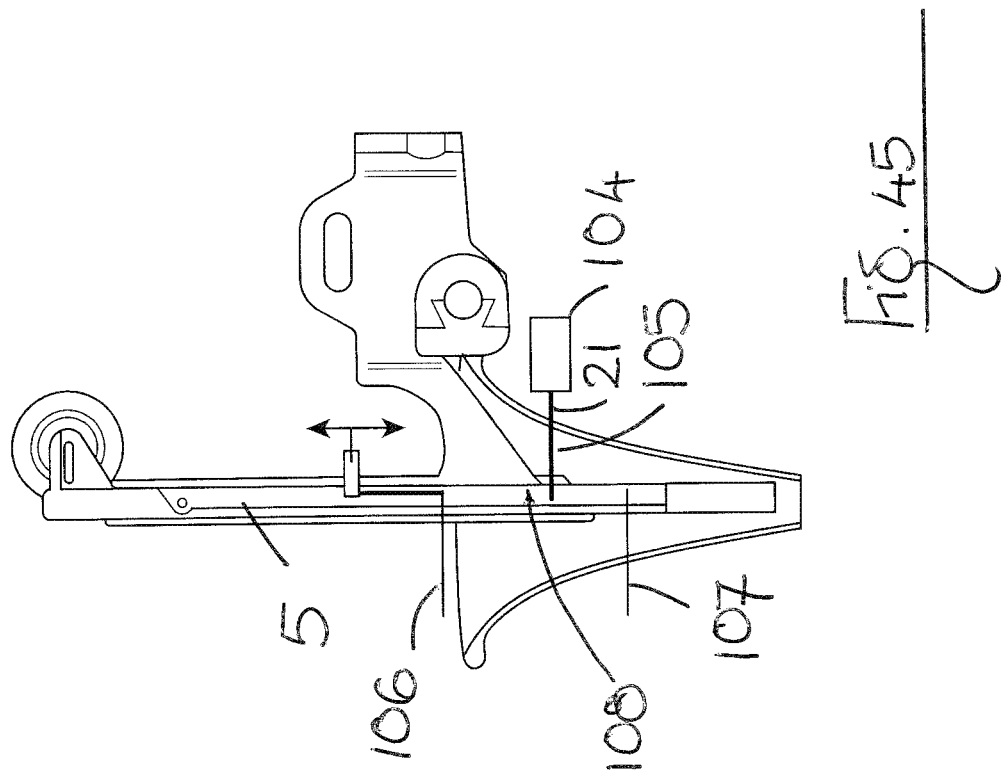
FIG. 45 is a side elevation of a further embodiment of the invention in which the scope is provided with a lockable depth control actuator mechanism in the form a lockable pin.

FIG. 45 is a side elevation of a further embodiment of the scope 1 of the invention in which the scope 1 is provided with a lockable depth control actuator mechanism 21 i.e. a safety lock 104 in the form a lockable pin 105 engageable with the probe 5. The pin 105 can be engaged to restrict the movement of the probe 5 up and down as determined by limits defined by lower and upper end points 106, 107 (i.e. upper and lower insertion limits of the probe 5) formed in a slot 108 defined in the probe 5. The upper and lower insertion limits can be set at a pre-determined position or can be varied with a limit adjuster 110. A spring may be used to set the lockable pin 105 in an always engaged position if desired.

The safety lock 104 can prevent accidental movement towards the tympanic membrane or middle ear and, in use, can be adjusted as required depending on anatomy (length width of ear canal).

Figure 46:
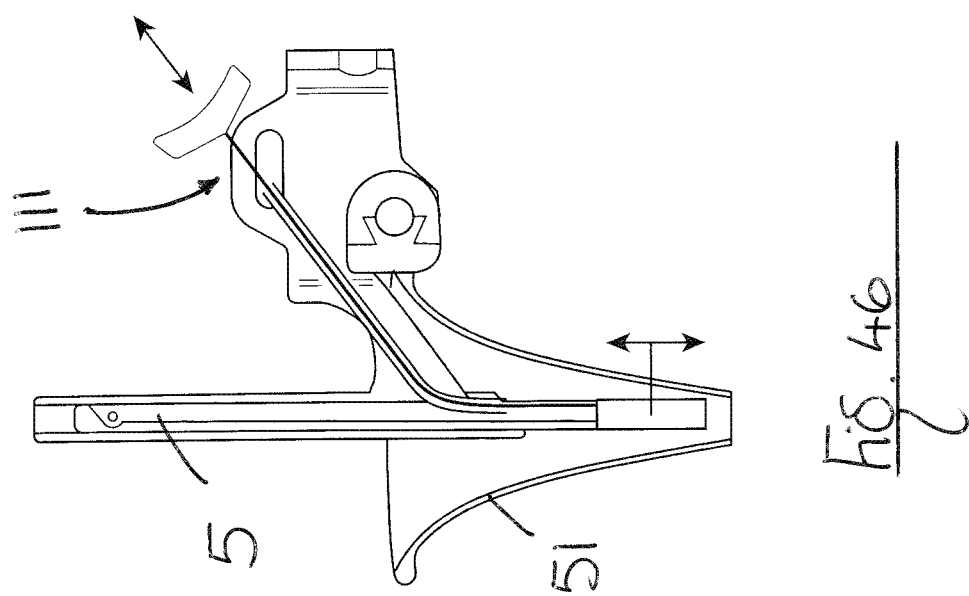
FIG. 46 is a side elevation of a further embodiment of the invention having a lockable depth control actuator mechanism in the form of a mechanical shutter release cable.

FIG. 46 is a side elevation of a still further embodiment of the invention having a lockable depth control actuator mechanism 21 or safety lock 104 in the form of a mechanical shutter release cable 111.

Figure 47:
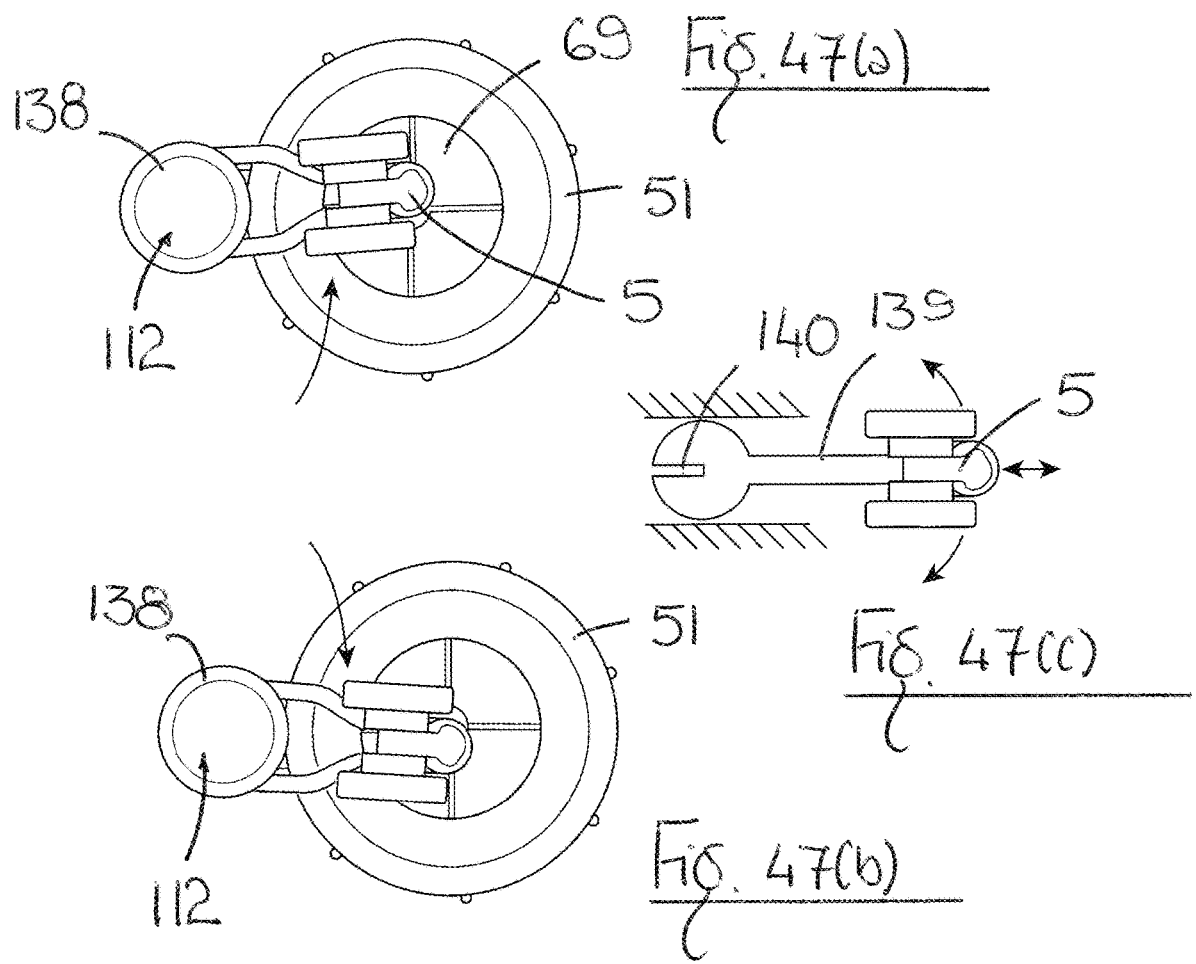
FIGS. 47(a) to 47(c) are top elevations of a further embodiment of the invention in which the probe is configured to be laterally movable (i.e. movable from side to side) within the speculum to accommodate surgical tools and enhance anatomical observation.

FIGS. 47(*a*) to 47(*b*) show top elevations of a further embodiment of the invention in which the probe 5 is configured to be laterally movable (i.e. swing an arc through a vertical axis at 112, from side to side) within the speculum 51 to accommodate surgical tools and enhance anatomical observations. This movement can be locked in place using a hand tightening nut 112. More particularly, as shown in FIG. 47(*c*) the probe 5 can enjoy planar movement in, out and side to side within the speculum 51 in the direction indicated by the arrows and can be locked into a particular position along a plane within the speculum by a planar arm lock 115 attached to the probe 5. The planar arm lock 115 has a cut 140 which allows it to be compressed into a planer slot, thus holding the unladen probe in position. Accordingly, the probe 5 is adapted to swing in an arc inside the speculum 51, or is movable to any position, in, out or from side to side (in the plane) inside the speculum 51. In another embodiment, not shown, the probe can swing in an arc through a horizontal axis, thus tilting side to side within the speculum.

Figure 48:
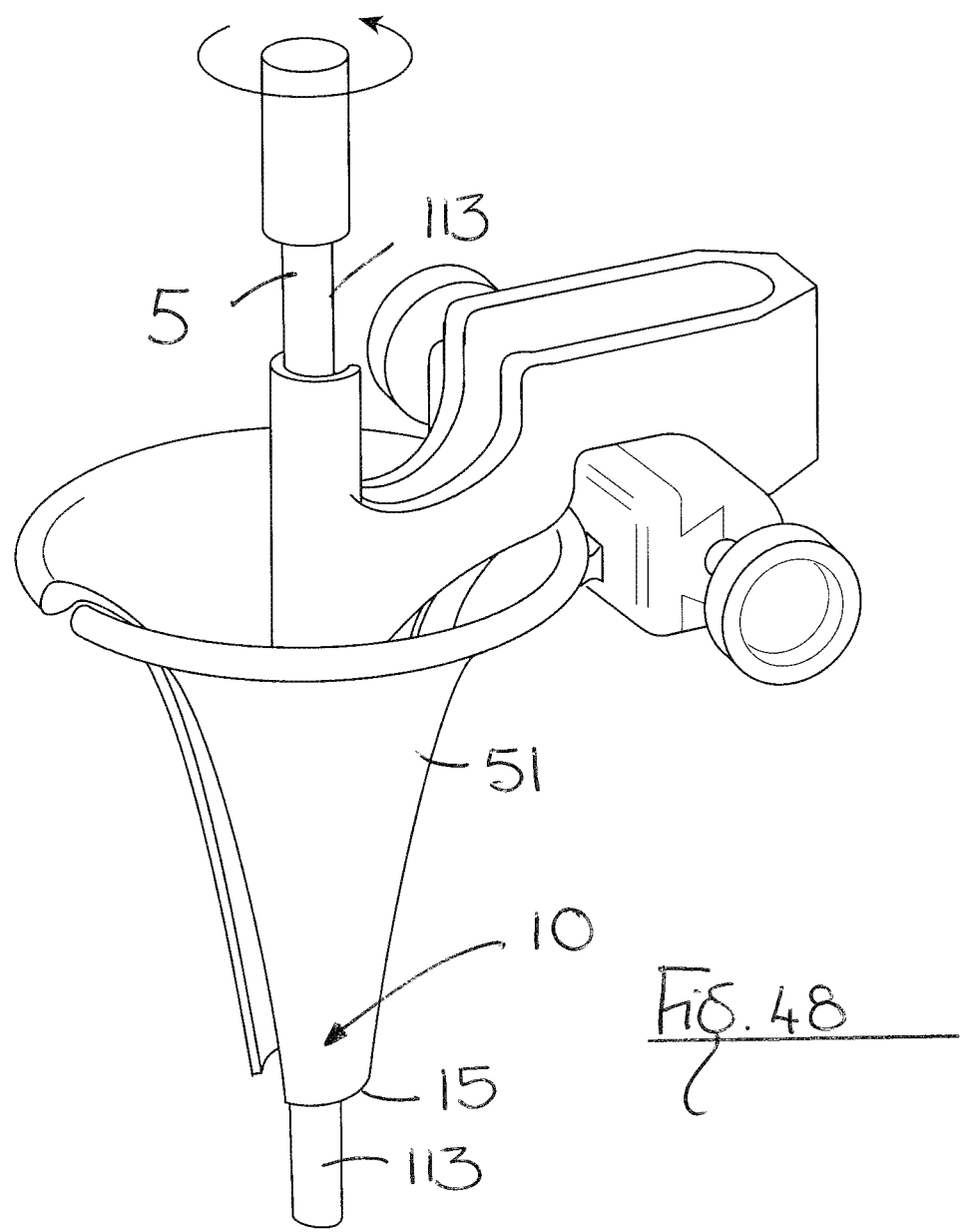
FIG. 48 is a perspective view from above and one side of a further embodiment of the invention in which the probe is a self-locking probe configured lock in position upon rotation about its longitudinal axis.

FIG. 48 shows a perspective view from above and one side of a further embodiment of the scope 1 of the invention in which the probe 5 is a rotatable self-locking probe 5 configured to lock in position upon rotation about its longitudinal axis. As shown in the drawings, the probe 5 is rotatable about its longitudinal axis in the direction indicated by the arrow to lock in position. A locking action can be achieved by providing the probe 5 with an elongate shaft 113 having a non-uniform cross-section defining locking relationship towards the distal open end 10 of the speculum 51 at the insertion opening 15.

In alternative embodiments, self-locking can be achieved via frictional engagement with the speculum 51 or through gear teeth disposed along the shaft 113 of the probe 5.

FIGS. 49 and 50 show a further embodiment of the invention in which probe mounting 18 is a hinged probe mounting 18 to allow for hinged removal of the probe 5 from the speculum 51 with the also being slidably removable from the speculum 51 in the direction indicated by the arrows whilst remaining attached to the scope 1. Hinged removal of the probe 5 from the speculum allows for placement of large items in the speculum 51 such as Tympanic Membrane graft material.

Figure 51:
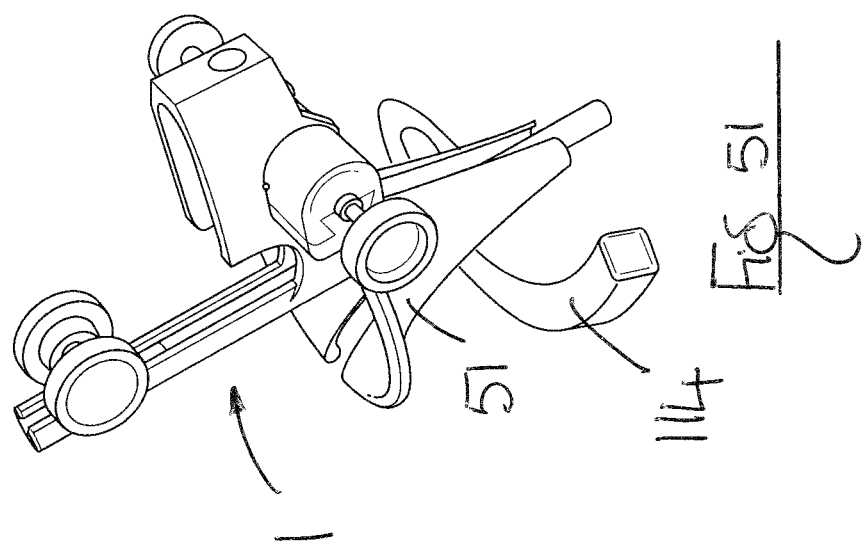
FIG. 51 is a perspective view from above and one side of an alternative embodiment of the invention in which the scope is provided with an ear clip or temple support so that the scope can be supported on an ear in the manner of a hearing aid or supported on a patient's temple.

FIG. 51 shows a perspective view from above and one side of an alternative embodiment of the invention in which the scope 1 is provided with an ear clip 114 attached to the speculum 51 so that the scope 1 can be supported on an ear in the manner of a hearing aid. In an alternative embodiment, the ear clip 114 can be replaced by a temple support so that the scope 1 can be supported on a patient's temple. The ear clip 114 or temple support can be formed from plastically deformable material.

Figure 52:
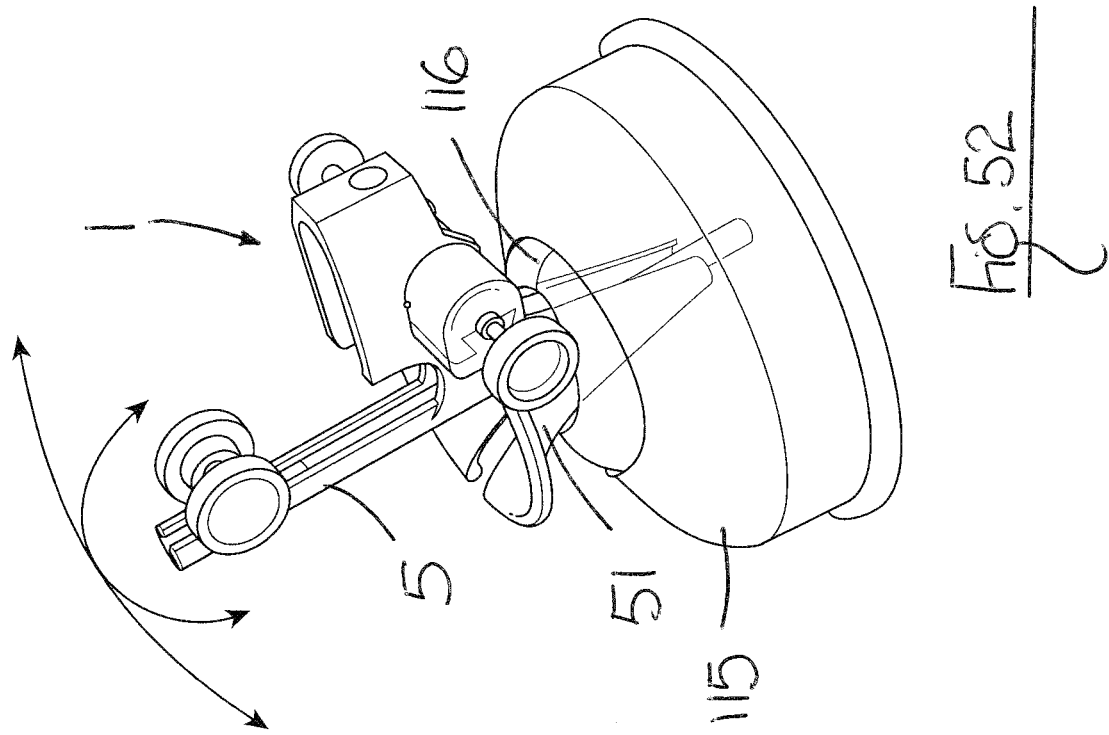
FIG. 52 is a perspective view from above and one side of an alternative embodiment of the invention in which the scope is provided with an ear cup to support the scope on an ear with a ball-joint to allow movement of the scope in the direction indicated by the arrows.

FIG. 52 shows a perspective view from above and one side of an alternative embodiment of the invention in which the scope 1 is provided with an ear cup 114 to support the scope on a patient's ear. A joint, which can be a ball-joint 116 is provided between the ear cup 114 and the speculum 51 to allow for ball-joint movement of the speculum 51 and probe 5 in the direction indicated by the arrows.

FIGS. 53 to 56 show a further embodiment of the invention in which the scope 1 is provided with a built-in camera cleaning unit 117 for cleaning the surface 118 of the camera 6. As shown in the drawings, the camera cleaning unit 117 is made up of blade or pad 119 which wipes/cleans the camera surface 118 as the probe 5 is moved from a proximal position towards the proximal end 9 of the speculum 51 (FIG. 54) towards and to the distal end 10 (FIGS. 55 and 56). The blade or pad 119 can be movable to pass over and clean the camera surface 118 and can be shaped and formed to ensure it makes contact with the camera surface 118 to restore visibility.

FIG. 57 shows a side elevation of a scope 1 of the invention with an alternative built-in camera cleaning unit 117 having a suction or irrigation channel 120 for directing fluid at the camera surface 118 or removing debris from the camera surface 118 with suction. If desired, cleaning fluid (e.g. saline) can be directed at the camera surface 118 via a directional baffle or channel 121 suitably angled adjacent the camera surface 118. The irrigation channel 120 can be integral with the scope 1 or can consist of a separate tool which is placed in the scope 1 to spray the camera 6.

FIG. 58 shows a side elevation of an alternative embodiment of the invention in which the built-in camera cleaning unit 117 is made up of a manually operable cleaning pad or brush which is slidable across the camera face 118. More particularly, the built-in camera cleaning unit is laterally slidable and is made up of a pad receiving recess 122 defined in the speculum 51 in which a cleaning pad or brush 123 is received. The cleaning pad or brush 123 is mechanically coupled to a manually operable cleaning control 124 which can optionally be operated by manual pulling and twisting to manipulate the pad 123 and clean the camera surface 118.

The data cable 8 can exert forces on the scope 1 as bending and torsional stiffness in the cable 8 can cause it to straighten—in practice the data cable 8 is seldom if ever straight in use. If these forces are neglected, scopes can become unstable in the ear making it difficult for the surgeon to control. In addition, data cables 8 can also have an effect on centre of gravity of the scope 1—in simple terms the unsupported mass of the data cable 8 should be offset in the scope 1 (as previously described) to maintain the centre of gravity with in the volume of the speculum 51.

If the cable has very low stiffness (so it cannot support its own weight) then the effect on the scope is negligible (coiled cables can display these properties). However, if this is not the case then strategies must be applied to the cable management to reduce these forces.

Figure 59:
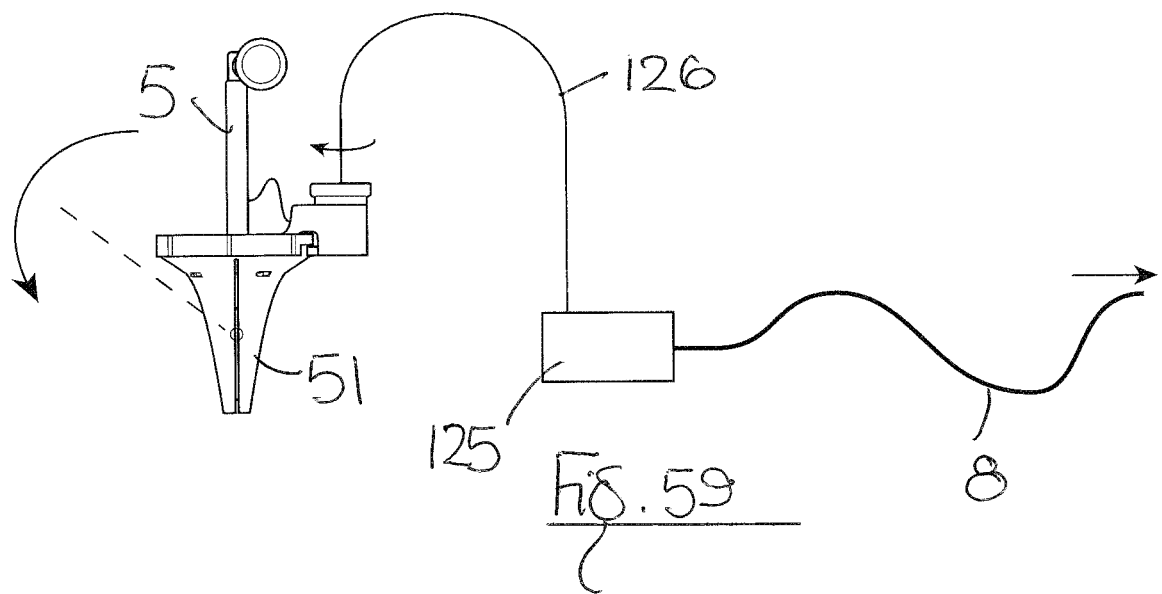
FIG. 59 is a side elevation of a further embodiment of the invention in which the data cable is provided with an anchor weight or point and an extended cable to minimise forces on the scope.

FIG. 59 shows a side elevation of a further embodiment of the invention in which the data cable 8 is provided with an anchor weight or point 125 and an extended cable indicated by the reference numeral 126 to minimise the above mentioned forces on the scope 1. The anchor weight 125 on the cable 8 prevents stiffness in the cable 8 between the anchor weight 125 and a stack/monitor from applying a destabilising force on the scope 1. If desired, the anchor weight 125 can sit or be attached on or beside a patient's head. In another embodiment, the anchor weight 125 can be movable.

Figure 60:
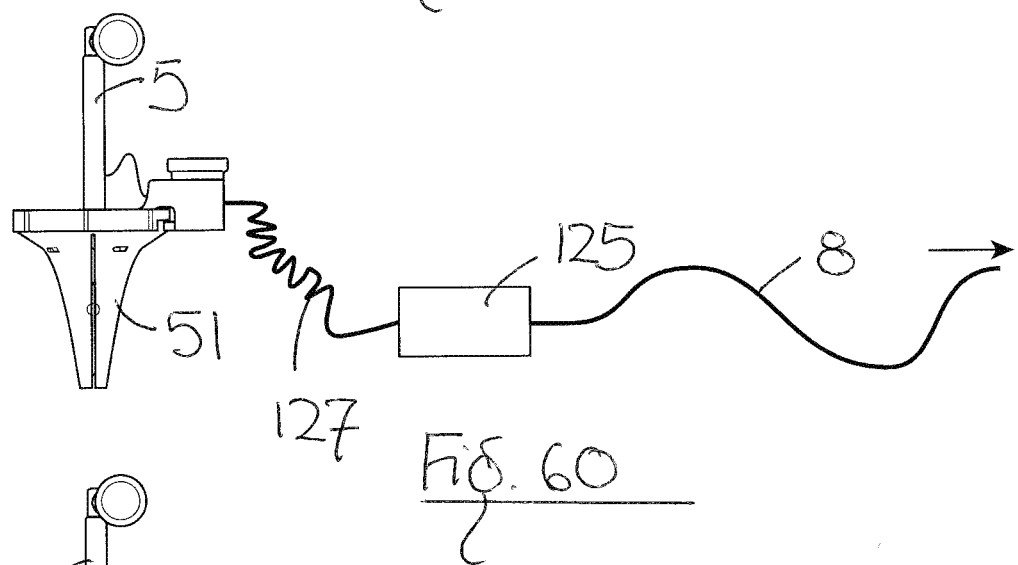
FIG. 60 is a side elevation of a further embodiment of the invention in which the data cable includes an anchor weight or point similar to FIG. 59, which also includes a coiled flexible cable to minimise forces on the scope.
Figure 61:
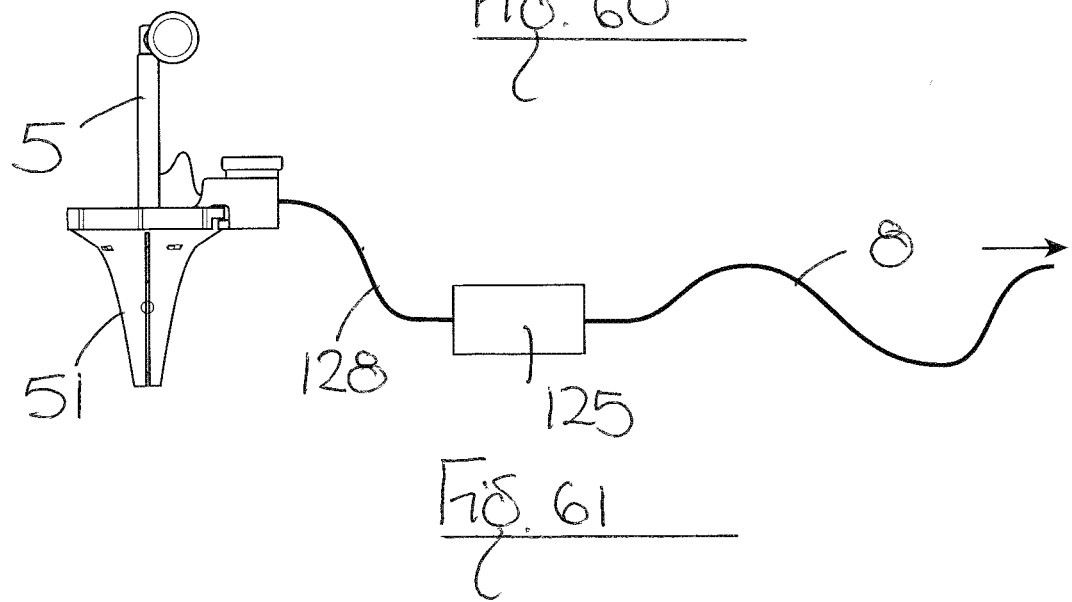
FIG. 61 is a side elevation of a further embodiment of FIG. 59 the data cable includes an anchor weight or point and a shape set cable to minimise forces on the scope.

As the data cable 8 between the anchor weight 125 and scope 1 may still exert a force on the scope 1, this can be further reduced by extending this cable as shown at 126 so that the stiffness exerts a lesser force. Alternatively, as shown in FIG. 60, the extended cable 126 can be replaced by a coiled flexible cable 127 to minimise forces on the scope 1. Alternatively, the coiled flexible cable 127 can be replaced by a shape set cable 128 as shown in FIG. 61 to minimise forces on the scope 1.

However, as will be appreciated by those skilled in the art, if data is delivered to the monitor/stack wirelessly, a cable is not required.

In another embodiment of the invention, the scope can be provided with built in rubber wipes to clean lenses while the scope 1 of the invention can be adapted for use with different sizes of speculum 51.

The scope of the invention can also employ two or more probes 5 as required or indeed two or more cameras 6 on a single probe 5. The cameras 6 can be positioned at different depths so that proximal camera can monitor instrument entry and a distal camera facilitate close viewing of surgery.

The scope 1 and systems of the invention can be formed from any suitable materials e.g. biodegradable materials.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A scope for examining or surgically treating ears comprising:
   at least one camera;
   a stabilizer for supporting the camera in or on the stabilizer, the stabilizer being configured to stabilize the scope in an ear canal wherein the scope is configured to maintain its center of gravity within a volume contained within the stabilizer, the stabilizer comprising a distal end and a proximal end having a greater weight towards its distal end thereby lowering the center of gravity of the scope towards the ear canal;
   a scope holder; and
   a headrest device for supporting a patient's head; wherein the headrest device is self-adjusting in response to patient head movement and comprises a headrest and a scope stand co-operable with the headrest to move in response to headrest movement to automatically reposition a scope held in the scope stand, and wherein the headrest comprises a convex lower face which allows the headrest to follow a patient's head movements.

2. A scope as claimed in claim 1, wherein the scope further comprises a light source being a direct light or a conduit piping in light.

3. A scope as claimed in claim 1, wherein the stabilizer comprises a speculum holder and a detachable or integrated speculum.

4. A scope as claimed in claim 3, wherein the speculum comprises a proximal open end, a distal insertion end, a substantially conical wall extending between the proximal open end and the distal end and the volume contained within the speculum is defined between the open end and the distal insertion end.

5. A scope as claimed in claim 4, wherein the speculum comprises a weight-balanced speculum configured to maintain a center of gravity towards the distal insertion end.

6. A scope as claimed in claim 5, wherein the weight-balanced speculum comprises increased weight below its center of gravity towards the distal insertion end.

7. A scope as claimed in claim 6, wherein the weight-balanced speculum comprises a combination of low-density and high-density material.

8. A scope as claimed in claim 7, wherein the high-density material is disposed towards the distal end of the speculum.

9. A scope as claimed in claim 3, wherein the center of gravity of the scope is located within the volume contained within the speculum by a balancing weight to balance the weight of the probe.

10. A scope as claimed in claim 9, wherein the balancing weight is attached to or integral with the speculum and/or the probe.

11. A scope as claimed in claim 3, wherein the speculum comprises a cut or cutaway portion through a sidewall of the speculum.

12. A scope as claimed in claim 3, wherein the speculum comprises two or more oppositely disposed cutaway portions or cuts through a sidewall of the speculum to define two or more expandable and contractable speculum blades.

13. A scope as claimed in claim 12, wherein the scope comprises an expansion mechanism to control movement of the blades.

14. A scope as claimed in claim 1, wherein: the camera is provided on a probe mountable on the stabilizer at a probe mounting; the probe mounting comprises a probe positioning mechanism; and the probe positioning mechanism comprises a probe sliding mechanism.

15. A scope as claimed in claim 14, wherein the probe sliding mechanism is configured to move the probe proximally and distally.

16. A scope as claimed in claim 1, wherein: the camera is provided on a probe mountable on the stabilizer at a probe mounting; the probe mounting comprises a probe positioning mechanism; and the probe positioning mechanism comprises a friction mounting defined between the stabilizer and the probe.

17. A scope as claimed in claim 16, wherein the probe is rotatably mountable in the probe mounting to change the angle of view of the camera.

18. A scope as claimed in claim 16, wherein the probe is detachable from the stabilizer.

19. A scope as claimed in claim 16, wherein the probe is laterally movable in the stabilizer in an in, out and side to side direction.

20. A scope as claimed in claim 1, wherein the scope further comprises a data cable and the data cable comprises an anchor weight to minimize forces on the scope.

21. A method of examining the external and middle ear during surgery, comprising: placing a scope into the ear canal, the scope comprising
   at least one camera and a stabilizer for supporting the camera in or on the stabilizer, the stabilizer being configured to stabilize the scope in the ear canal wherein the scope is configured to maintain its center of gravity within a volume contained within the stabilizer during treatment, the stabilizer comprising a distal end and a proximal end having a greater weight towards its distal end thereby lowering the center of gravity of the scope towards the ear canal;
   employing a dynamic two-handed technique; and
   viewing a camera feed from the scope while retaining the scope within the ear canal.

22. The method of claim 21, wherein the scope is used while a surgeon using the scope holds two surgical tools at the same time.

23. The method of claim 22, wherein the tools comprise at least two of: suctions; cutting tools; irrigation tools, perforation tools; holding tools; forceps; drills; lasers; and surgical curettes.

24. The method of claim 21, wherein the stabilizer comprises a speculum.

25. The method of claim 24, further comprising a step of adjusting the size of the speculum after the scope is placed to allow maximum operating space.

26. The method of claim 25, wherein the size of the speculum is adjusted by using an adjustable speculum which allows the user to expand the speculum within the ear canal.

27. The method of claim 21, further comprising movement of the probe to allow maximum operating space for placing tools on both sides of the probe or multiple tools on one side.

* * * * *